(12) United States Patent
Mitchell et al.

(10) Patent No.: US 8,329,701 B2
(45) Date of Patent: Dec. 11, 2012

(54) DIHYDROFURO PYRIMIDINES AS AKT PROTEIN KINASE INHIBITORS

(75) Inventors: Ian S. Mitchell, Lafayette, CO (US); James F. Blake, Longmont, CO (US); Rui Xu, Longmont, CO (US); Nicholas C. Kallan, Boulder, CO (US); Dengming Xiao, Longmont, CO (US); Keith Lee Spencer, Lyons, CO (US); Josef R. Bencsik, Longmont, CO (US)

(73) Assignee: Array Biopharma Inc., Boulder, CO (US)

( * ) Notice: Subject to any disclaimer, the term of this patent is extended or adjusted under 35 U.S.C. 154(b) by 673 days.

(21) Appl. No.: 12/307,537

(22) PCT Filed: Jul. 5, 2007

(86) PCT No.: PCT/US2007/072863
§ 371 (c)(1),
(2), (4) Date: Dec. 7, 2009

(87) PCT Pub. No.: WO2008/006025
PCT Pub. Date: Jan. 10, 2008

(65) Prior Publication Data
US 2011/0269773 A1      Nov. 3, 2011

Related U.S. Application Data

(60) Provisional application No. 60/818,807, filed on Jul. 6, 2006.

(51) Int. Cl.
| A61K 31/519 | (2006.01) |
| A61P 29/00 | (2006.01) |
| A61P 17/00 | (2006.01) |
| A61P 9/00 | (2006.01) |
| A61P 25/28 | (2006.01) |
| A61P 15/00 | (2006.01) |
| A61P 35/00 | (2006.01) |
| C07D 491/048 | (2006.01) |

(52) U.S. Cl. .................. 514/252.16; 544/278
(58) Field of Classification Search .............. None
See application file for complete search history.

(56) References Cited

U.S. PATENT DOCUMENTS

| 3,885,035 A | 5/1975 | Simpson |
| 3,956,495 A | 5/1976 | Lacefield |
| 3,966,936 A | 6/1976 | Cronin et al. |
| 4,060,615 A | 11/1977 | Matier et al. |
| 4,352,928 A | 10/1982 | Hiranuma et al. |
| 5,051,412 A | 9/1991 | Macor |
| 5,525,625 A | 6/1996 | Bridges et al. |
| 5,563,152 A | 10/1996 | Kulagowski et al. |
| 5,610,303 A | 3/1997 | Kimura et al. |
| 5,750,531 A | 5/1998 | Lee et al. |
| 5,750,545 A | 5/1998 | Akahoshi et al. |
| 5,817,671 A | 10/1998 | Filla et al. |
| 6,310,060 B1 | 10/2001 | Barrett et al. |
| 6,423,716 B1 | 7/2002 | Matsuno et al. |
| 6,469,004 B1 | 10/2002 | Barrett et al. |
| 6,506,798 B1 | 1/2003 | Barrett et al. |
| 6,627,628 B1 | 9/2003 | Schindler et al. |
| 6,831,175 B2 | 12/2004 | Li et al. |
| 7,041,687 B2 | 5/2006 | Binch et al. |
| 7,067,664 B1 | 6/2006 | Chen |
| 7,115,741 B2 | 10/2006 | Levy et al. |
| 7,125,880 B1 | 10/2006 | Chen |
| 7,223,738 B2 | 5/2007 | Bilodeau et al. |
| 7,223,767 B2 | 5/2007 | Clark et al. |
| 2003/0004193 A1 | 1/2003 | Barrett et al. |
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0199511 A1 | 10/2003 | Li et al. |
| 2003/0216460 A1 | 11/2003 | Wallace et al. |

(Continued)

FOREIGN PATENT DOCUMENTS

EP           194161           9/1986

(Continued)

OTHER PUBLICATIONS

Database accession No. 147:166330 abstract, Database CAPLUS, Chemical Abstracts Service, Columbus Ohio, US, Retrieved from STN accession No. 2007:711051, 2007, 1 page.
D'Souza et al., "(R)–(+)–3-Amino-2-phenylpropanoic Acid: a Revised Absolute Configureation based on an Enantioselective Synthesis and an X-Ray Crystal Structure of the Salt with (1S)–(+)–Camphor-10-sulfonic Acid", J. Chem. Soc. Perkins Trans. 1, 2 pages, (1995).
Li, Qun "Expert Opinion: Recent Progress in the Discovery of Akt Inhibitors as Anticancer Agents", Informa Healthcare, 2007, 17(9), pp. 1077-1130.
Ohno, S., et al., "Synthesis and Hypoglycemic Activity of 7,8-Dihydro-6H-thiopyrano[3,2-d]pyrimidine Derivatives and Related Compounds", Chem. Pharm. Bull., 1986, 34(10), 4150-4165.
Patent Cooperation Treaty, "International Search Report and Written Opinion of the International Searching Authority", PCT/US2007/072885, Dec. 3, 2007, 10 pages.

(Continued)

Primary Examiner — Bong-Sook Baek
(74) Attorney, Agent, or Firm — Viksnins Harris & Padys PLLP

(57) ABSTRACT

The present invention provides compounds, including resolved enantiomers, diastereomers, solvates and pharmaceutically acceptable salts thereof, comprising the Formula (I): Also provided are methods of using the compounds of this invention as AKT protein kinase inhibitors and for the treatment of hyperproliferative diseases such as cancer.

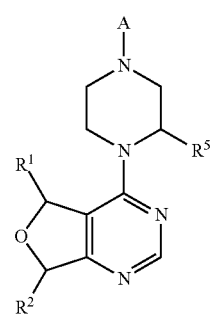

(I)

27 Claims, No Drawings

U.S. PATENT DOCUMENTS

| | | | |
|---|---|---|---|
| 2003/0232869 A1 | 12/2003 | Wallace et al. |
| 2004/0053933 A1 | 3/2004 | Pontillo et al. |
| 2004/0102360 A1 | 5/2004 | Barnett et al. |
| 2004/0116710 A1 | 6/2004 | Wallace et al. |
| 2004/0176400 A1 | 9/2004 | Capelli et al. |
| 2005/0059687 A1 | 3/2005 | Makings et al. |
| 2005/0130954 A1 | 6/2005 | Mitchell et al. |
| 2005/0182061 A1 | 8/2005 | Green et al. |
| 2006/0025074 A1 | 2/2006 | Liang et al. |
| 2006/0062400 A1 | 3/2006 | Chia-Chun |
| 2007/0004708 A1 | 1/2007 | Andreotti et al. |
| 2007/0027156 A1 | 2/2007 | Nakai et al. |
| 2007/0135466 A1 | 6/2007 | Ledeboer et al. |
| 2008/0076774 A1 | 3/2008 | Anand et al. |
| 2008/0188482 A1 | 8/2008 | Rice et al. |
| 2010/0168123 A1 | 7/2010 | Mitchell et al. |

FOREIGN PATENT DOCUMENTS

| | | |
|---|---|---|
| WO | WO 95/03286 | 2/1995 |
| WO | WO 98/43960 | 10/1998 |
| WO | WO 99/01421 | 1/1999 |
| WO | WO 99/01426 | 1/1999 |
| WO | WO 00/40235 | 7/2000 |
| WO | WO 00/40237 | 7/2000 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/68201 | 11/2000 |
| WO | WO 01/05390 | 1/2001 |
| WO | WO 01/05391 | 1/2001 |
| WO | WO 01/05392 | 1/2001 |
| WO | WO 01/05393 | 1/2001 |
| WO | WO 01/68619 | 9/2001 |
| WO | WO 02/06213 | 1/2002 |
| WO | WO 02/18319 | 3/2002 |
| WO | WO 02/44166 | 6/2002 |
| WO | WO 02/083139 | 10/2002 |
| WO | WO 03/022214 | 3/2003 |
| WO | WO 03/064397 | 8/2003 |
| WO | WO 03/077855 | 9/2003 |
| WO | WO 03/077914 | 9/2003 |
| WO | WO 03/086279 | 10/2003 |
| WO | WO 03/086394 | 10/2003 |
| WO | WO 03/086403 | 10/2003 |
| WO | WO 03/086404 | 10/2003 |
| WO | WO 03/094918 | 11/2003 |
| WO | WO 2004/041162 | 5/2004 |
| WO | WO 2004/096130 | 11/2004 |
| WO | WO 2005/014558 | 2/2005 |
| WO | WO 2005/117909 | 12/2005 |
| WO | WO 2006/027346 | 3/2006 |
| WO | WO 2006/046023 | 5/2006 |
| WO | WO 2006/071819 | 7/2006 |
| WO | WO 2006/090261 | 8/2006 |
| WO | WO 2006/136830 | 12/2006 |
| WO | WO 2007/042298 | 4/2007 |
| WO | WO 2007/077961 | 7/2007 |
| WO | WO 2007/125320 | 11/2007 |
| WO | WO 2008/003697 | 1/2008 |
| WO | WO 2008/003958 | 1/2008 |
| WO | WO 2008/003978 | 1/2008 |
| WO | WO 2008/005511 | 1/2008 |
| WO | WO 2008/005964 | 1/2008 |
| WO | WO 2008/006032 | 1/2008 |
| WO | WO 2008/006040 | 1/2008 |
| WO | WO 2008/012635 | 1/2008 |

OTHER PUBLICATIONS

Ross, L., et al., "Potential Anticancer Agents. XVIII. Synthesis of Substituted 4,5-Trimethylenepyrimidines", J. Am. Chem. Soc., 1959, 81, 3108-3113.

Thomas, S. A., "Identification of a novel 3,5-disubstituted pyridine as a potent, selective, and orally active inhibitor of Akt1 kinase", Bioorg. Med. Chem. Lett., 2006, 16, 3740-3744.

Truong, T. N., "Office Action for U.S. Appl. No. 10/993,173", United States Patent and Trademark Office, Aug. 6, 2008, 8 pages.

Truong, T. N., "Office Action for U.S. Appl. No. 10/993,173", United States Patent and Trademark Office, May 26, 2009, 8 pages.

Usuelli, A., Primary Examiner, "European Office Action for Application No. 07799326.9", European Patent Office, Nov. 26, 2009, 3 pages.

Vippagunta, S.R., (Adv. Drug. Delivery Rev., 2001, 48, pp. 3-26).

Zhao, Z., et al., "Discovery of 2,3,5-trisubstituted pyridine derivatives as potent Akt1 and Akt2 dual inhibitors", Bioorg. Med. Chem. Lett., 2005, 15, 905-909.

Zhu, G., "Discovery and SAR of oxindole-pyridine-based protein kinase B/Akt inhibitors for treating cancers", Bioorg. Med. Chem. Lett., 2006, 16, 3424-3429.

DIHYDROFURO PYRIMIDINES AS AKT PROTEIN KINASE INHIBITORS

PRIORITY OF INVENTION

This application claims priority to U.S. Provisional Application No. 60/818,807 that was filed on 6 Jul. 2006, which is hereby incorporated herein by reference in its entirety.

BACKGROUND OF THE INVENTION

1. Field of the Invention

This invention relates to novel inhibitors of serine/threonine protein kinases (e.g., AKT and related kinases), pharmaceutical compositions containing the inhibitors, and methods for preparing these inhibitors. The inhibitors are useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protooncogene v-akt of the acutely transforming retrovirus AKT8. Due to its high sequence homology to protein kinases A and C, Akt is also called Protein Kinase B (PKB) and Related to A and C (RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)$P_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689). Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

SUMMARY OF THE INVENTION

This invention provides novel compounds that inhibit AKT protein kinases. The compounds of the present invention have utility as therapeutic agents for diseases and conditions that can be treated by the inhibition of AKT protein kinases. More specifically, the present invention includes compounds having the general Formula I:

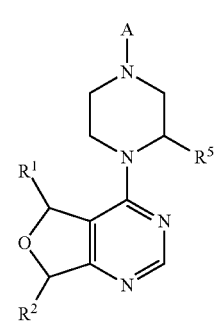

and tautomers, resolved enantiomers, resolved diastereomers, solvates, metabolites, salts and pharmaceutically acceptable prodrugs thereof, wherein $R^1$, $R^2$, $R^5$ and A are as defined herein.

The invention also provides pharmaceutical compositions comprising a compound of Formula I, or a solvate, metabolite, or pharmaceutically acceptable salt or prodrug thereof.

In a further aspect, the present invention provides a method of treating diseases or medical conditions in a mammal mediated by AKT protein kinases, comprising administering to said mammal one or more compounds of Formula I, or a solvate, metabolite, or pharmaceutically acceptable salt or prodrug thereof, in an amount effective to treat or prevent said disorder. AKT protein kinase mediated conditions that can be treated according to the methods of this invention include, but are not limited to, inflammatory, hyperproliferative, cardiovascular, neurodegenerative, gynecological, and dermatological diseases and disorders.

In a further aspect, the present invention provides a method of inhibiting the production of AKT protein kinases in a mammal, which comprises administering to said mammal a compound of Formula I, or a solvate, metabolite, or pharmaceutically acceptable salt or prodrug thereof in an amount effective to inhibit production of an AKT protein kinase.

In a further aspect, the present invention provides methods of inhibiting the activity of AKT protein kinases, comprising contacting said kinase with a compound of Formula I.

The inventive compounds may be used advantageously in combination with other known therapeutic agents. Accordingly, this invention also provides pharmaceutical compositions comprising a compound of Formula I or a solvate, metabolite, or pharmaceutically acceptable salt or prodrug thereof, in combination with a second therapeutic agent.

This invention also provides compounds of Formula I and solvates, metabolites, and pharmaceutically acceptable salts and prodrugs thereof for use as medicaments in the treatment of AKT protein kinase-mediated conditions.

An additional aspect of the invention is the use of a compound of Formula I, or a solvate, metabolite, or pharmaceutically acceptable salt or prodrug thereof, for therapy. In one embodiment, the therapy comprises the treatment of an AKT protein kinase-mediated condition.

This invention further provides kits for the treatment of an AKT protein kinase-mediated disease or disorder, said kit comprising a compound of Formula I, or a solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 2,2-dimethylpropyl ($CH_2C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), 1-propenyl, 1-buten-1-yl, 1-buten-2-yl, and the like.

The term "alkynyl" as used herein refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$C≡CH).

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently with one or more substituents described herein.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "hetercyclyl" and "heterocyclic ring" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" as used herein means fluoro, chloro, bromo or iodo.

The term "a" as used herein means one or more.

As used herein, the terms "compound of this invention," "compounds of the present invention" and "compounds of Formula I" includes compounds of Formula I and tautomers, resolved enantiomers, resolved diastereomers, racemic mixtures, solvates, metabolites, salts (including pharmaceutically acceptable salts) and pharmaceutically acceptable prodrugs thereof.

In general, the various moieties or functional groups of the compounds of Formula I may be optionally substituted by one or more substituents. Examples of substituents suitable for purposes of this invention include, but are not limited to, halogen, alkyl, alkenyl, alkynyl, cycloalkyl, heterocycloalkyl, OR, NO$_2$, CN, CO$_2$R, (C=O)R, O(C=O)R, SR, SOR, SO$^2$R, aryl, heteroaryl, (C=O)NR$^2$R$^3$, NR$^2$R$^3$, NR(C=O)R, SO$_2$NR$^2$R$^3$, PO$_3$H$_2$, and SO$_3$H$_2$, where R, R$^2$ and R$^3$ are alkyl, alkenyl, alkynyl, cycloalkyl, heterocyclyl, aryl or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

AKT Inhibitors

The inventive compounds of Formula I are useful for inhibiting AKT protein kinases. The compounds of Formula I may also be useful as inhibitors of tyrosine kinases as well as serine and threonine kinases in addition to AKT. Such compounds have utility as therapeutic agents for diseases that can be treated by the inhibition of the AKT protein kinase signaling pathway and tyrosine and serine/threonine kinase receptor pathways.

In general, the invention includes compounds of the Formula I:

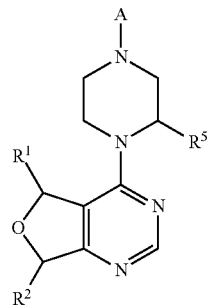

and tautomers, resolved enantiomers, resolved diastereomers, solvates, metabolites, salts and pharmaceutically acceptable prodrugs thereof, wherein:

$R^1$ is H, methyl, ethyl, propyl, isopropyl, cyclopropyl, $CF_3$, $CHF_2$ or $CH_2F$;

$R^2$ is H or Me;

$R^5$ is H, Me, Et, or $CF_3$;

A is

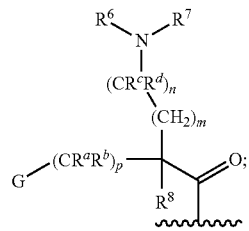

G is phenyl optionally substituted independently with one to four $R^9$ groups;

$R^6$ and $R^7$ are independently H, ($C_3$-$C_6$ cycloalkyl)-($CH_2$), ($C_3$-$C_6$ cycloalkyl)-($CH_2CH_2$), V—($CH_2$)$_{0-1}$ wherein V is a 5-6 membered heteroaryl, W—($CH_2$)$_{1-2}$ wherein W is phenyl optionally substituted with F, Cl, Br, I, OMe, $CF_3$ or Me, $C_3$-$C_6$-cycloalkyl, hydroxy-($C_3$-$C_6$-cycloalkyl), fluoro-($C_3$-$C_6$-cycloalkyl), $CH(CH_3)CH(OH)$phenyl, 4-6 membered heterocycle optionally substituted with F, OH, cyclopropylmethyl, $C_1$-$C_3$ alkyl or C(=O)($C_1$-$C_3$ alkyl) or $C_1$-$C_6$-alkyl optionally substituted with one or more groups independently selected from OH, O($C_1$-$C_6$-alkyl), CN, F, $NH_2$, NH($C_1$-$C_6$-alkyl), N($C_1$-$C_6$-alkyl)$_2$, tetrahydropyranyl, tetrahydrofuranyl, morpholinyl, oxetanyl, piperidinyl, and pyrrolidinyl, or $R^6$ and $R^7$ together with the nitrogen to which they are attached form a 4-6 membered heterocyclic ring optionally substituted with one or more groups independently selected from OH, halogen, oxo, $CF_3$, $CH_2CF_3$, and ($C_1$-$C_3$)alkyl;

$R^a$ and $R^b$ are H, or $R^a$ is H, and $R^b$ and $R^6$ together with the atoms to which they are attached form a 5-6 membered heterocyclic ring having one or two ring nitrogen atoms;

$R^c$ and $R^d$ are H or Me, or $R^c$ and $R^d$ together with the atom to which they are attached form a cyclopropyl ring;

$R^8$ is H, Me, or OH, or $R^8$ and $R^6$ together with the atoms to which they are attached form a 5-6 membered heterocyclic ring having one or two ring nitrogen atoms;

each $R^9$ is independently halogen, $C_1$-$C_6$-alkyl, $C_3$-$C_6$-cycloalkyl, O—($C_1$-$C_6$-alkyl), $CF_3$, $OCF_3$, S($C_1$-$C_6$-alkyl), CN, $OCH_2$-phenyl, $NH_2$, NH—($C_1$-$C_6$-alkyl), N—($C_1$-$C_6$-alkyl)$_2$, piperidine, pyrrolidine, $CH_2F$, $CHF_2$, $OCH_2F$, $OCHF_2$, OH, $SO_2$($C_1$-$C_6$-alkyl), C(O)$NH_2$, C(O)NH($C_1$-$C_6$-alkyl), and C(O)N($C_1$-$C_6$-alkyl)$_2$; and m, n and p are independently 0 or 1.

In a further embodiment, $R^6$ and $R^7$ are independently H, ($C_3$-$C_6$ cycloalkyl)-($CH_2$), ($C_3$-$C_6$ cycloalkyl)-($CH_2CH_2$), V—($CH_2$)$_{0-1}$ wherein V is a 5-6 membered heteroaryl, W—($CH_2$)$_{1-2}$ wherein W is phenyl optionally substituted with F, Cl or Me, $C_3$-$C_6$-cycloalkyl, hydroxy-($C_3$-$C_6$-cycloalkyl), fluoro-($C_3$-$C_6$-cycloalkyl), $CH(CH_3)CH(OH)$phenyl, or $C_1$-$C_6$-alkyl optionally substituted with one or more groups independently selected from OH, O($C_1$-$C_6$-alkyl), CN, F, $NH_2$, NH($C_1$-$C_6$-alkyl), N($C_1$-$C_6$-alkyl)$_2$, piperidinyl, and pyrrolidinyl, or $R^6$ and $R^7$ together with the nitrogen to which they are attached form a 4-6 membered heterocyclic ring optionally substituted with one or more groups independently selected from OH, halogen, oxo, $CF_3$, $CH_2CF_3$, and ($C_1$-$C_3$)alkyl.

Referring to the G group of Formula I, examples include phenyl optionally substituted with one or more $R^9$ groups independently selected from F, Cl, Br, CN, methyl, ethyl, isopropyl, $OCH_3$, $OCH_2CH_3$, $CF_3$, $OCF_3$, $SCH_3$, $OCH_2Ph$ and cyclopropyl. Exemplary embodiments include, but are not limited to, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 2-trifluoromethylphenyl, 3-trifluoromethylphenyl, 4-trifluoromethylphenyl, 2-cyanophenyl, 3-cyanophenyl, 4-cyanophenyl, 2-methoxyphenyl, 3-methoxyphenyl, 4-methoxyphenyl, 2-ethoxyphenyl, 3-ethoxyphenyl, 4-ethoxyphenyl, 2-thiomethylphenyl, 3-thiomethylphenyl, 4-thiomethylphenyl, 2-trifluoromethoxyphenyl, 3-trifluoromethoxyphenyl, 4-trifluoromethoxyphenyl, 2-cyclopropylphenyl, 3-cyclopropylphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5- difluoro-4-chlorophenyl, 3,5-difluoro-4-bromophenyl, 2,3-difluoro-4-bromophenyl, 2,5-difluoro-4-bromophenyl and 4-(OCH$_2$Ph)-phenyl.

Referring to the R$^6$ and R$^7$ groups of Formula I, the term "(C$_3$-C$_6$-cycloalkyl)-(CH$_2$)" includes groups such as, but not limited to, cyclopropyl-CH$_2$, cyclobutyl-CH$_2$, cyclopentyl-CH$_2$, and cyclohexyl-CH$_2$.

Referring to the R$^6$ and R$^7$ groups of Formula I, the term "V—(CH$_2$)$_{0-1}$" includes groups wherein V is a 5-6 membered heteroaryl having from one to two ring heteroatoms independently selected from N, O and S. Exemplary groups include, but are not limited to, the following structures:

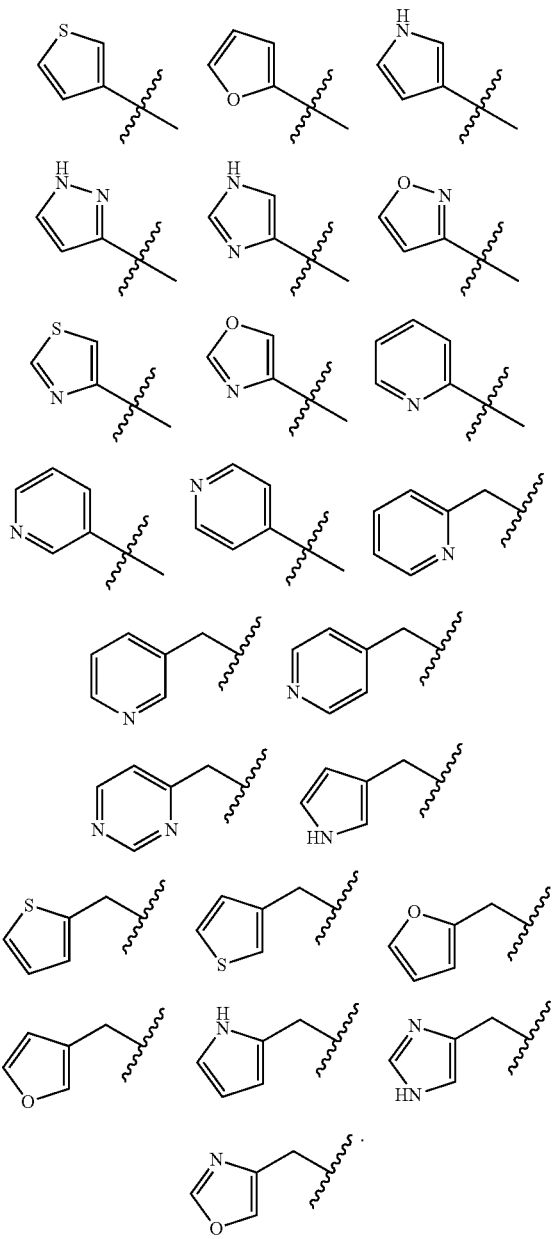

Referring to the R$^6$ and R$^7$ groups of Formula I, the term "hydroxy-(C$_3$-C$_6$-cycloalkyl)" includes, but is not limited to, the following structures:

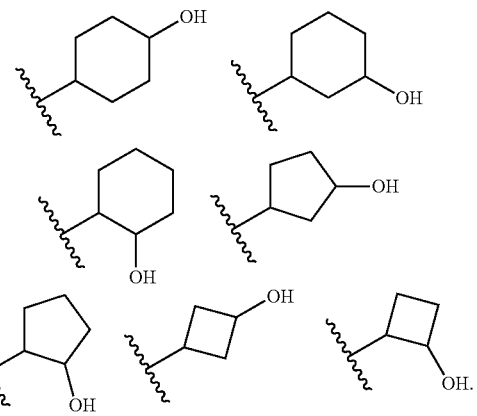

Referring to the R$^6$ and R$^7$ groups of Formula I, the phrase "C$_1$-C$_6$-alkyl optionally substituted with one or more groups independently selected from OH, OMe, and CN" includes, but is not limited to, CH$_2$OH, CH$_2$CH$_2$OH, CH$_2$CH$_2$CH$_2$OH, CH$_2$CH(OH)CH$_2$, CH$_2$CH$_2$CH(OH)CH$_3$, CH$_2$C(OH)(CH$_3$)$_2$, CH$_2$OMe, CH$_2$CH$_2$OMe, CH$_2$CH$_2$CH$_2$OMe, CH$_2$CH(OMe)CH$_2$, CH$_2$CH$_2$CH(OMe)CH$_3$, CH$_2$C(OMe)(CH$_3$)$_2$, CH$_2$CN, CH$_2$CH$_2$CN, CH$_2$CH$_2$CH$_2$CN, CH$_2$CH(CN)CH$_2$, CH$_2$CH$_2$CH(CN)CH$_3$, CH$_2$C(CN)(CH$_3$)$_2$, and the like.

Referring to the R$^6$ and R$^7$ groups of Formula I, in certain embodiments the term "heteroaryl" refers to a 5-6 membered heteroaryl having from one to two ring heteroatoms independently selected from N, O and S.

Referring to the R$^6$ and R$^7$ groups of Formula I or Ia, the phrase "R$^6$ and R$^7$ together with the nitrogen to which they are attached form a 4-6 membered heterocyclic ring optionally substituted with one or more groups independently selected from OH, halogen, oxo, CF$_3$, CH$_2$CF$_3$, and (C$_1$-C$_3$)alkyl" includes but is not limited to the following structures:

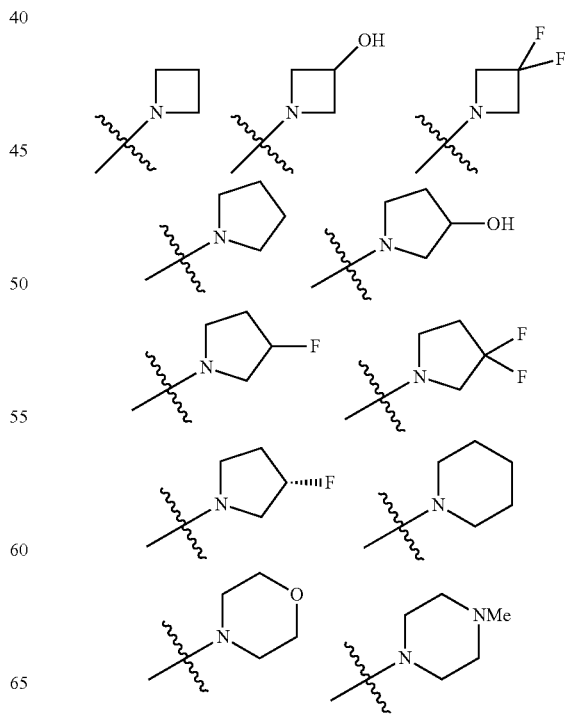

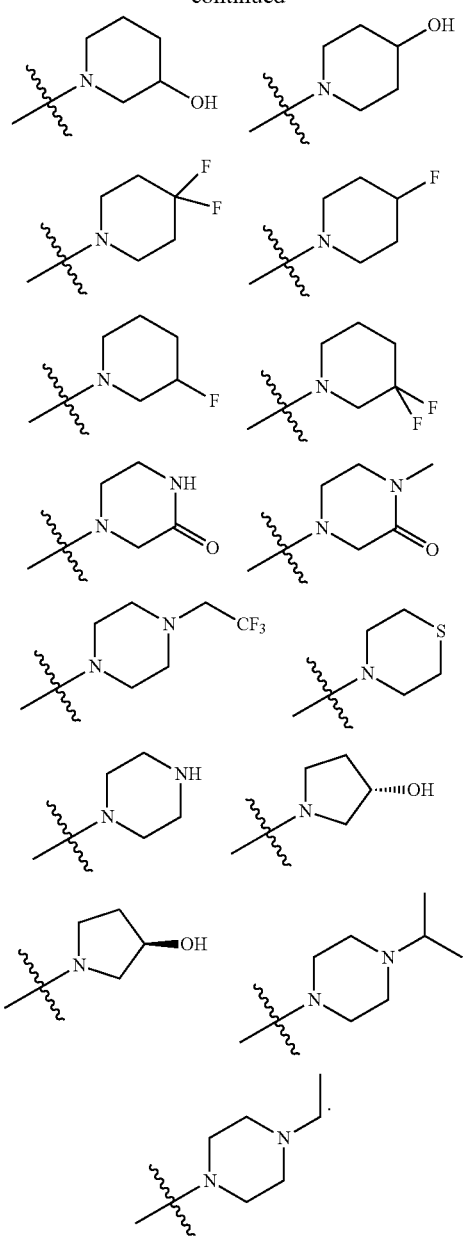
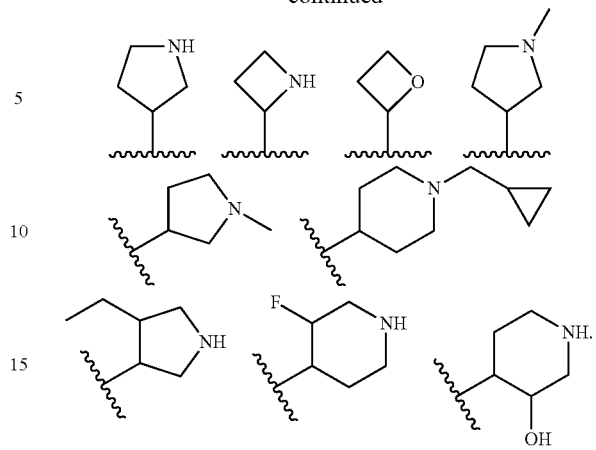

Referring to the $R^6$ and $R^7$ groups of Formula I or Ia, the phrase "4-6 membered heterocycle optionally substituted with F, OH, cyclopropylmethyl, $C_1$-$C_3$ alkyl or C(=O)($C_1$-$C_3$ alkyl)" includes but is not limited to the following structures:

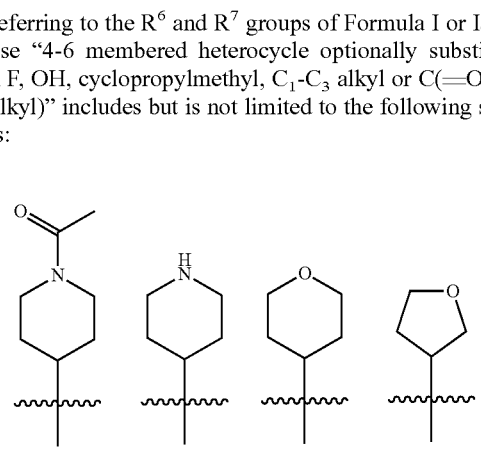

In one embodiment of Formula I, $R^1$ is methyl, wherein $R^1$ is optionally in the (R) or (S) configuration. In another embodiment of Formula I, $R^1$ is H.

In one embodiment of Formula I, $R^2$ is H.

In one embodiment of Formula I, $R^5$ is H or methyl. In another embodiment, $R^5$ is methyl, wherein $R^5$ is optionally in the (S) configuration.

In one embodiment of Formula I, G is phenyl optionally substituted with one to three $R^9$ groups independently selected from F, Cl, Br, CN, methyl, ethyl, isopropyl, $CF_3$, $OCF_3$, SMe, OMe, and $OCH_2Ph$. Examples include, but are not limited to, phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl, 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl and 4-($OCH_2Ph$)-phenyl.

In particular embodiments, G is 4-chlorophenyl, 2,4-dichlorophenyl, 4-chloro-3-fluorophenyl, 4-fluorophenyl, 3,4-difluorophenyl, 4-methylphenyl, 4-methoxyphenyl or 4-($OCH_2Ph$)-phenyl.

In certain embodiments, G is a 9 membered heteroaryl. In particular embodiments, G is an indole.

In particular embodiments, $R^6$ and $R^7$ are independently H.

In particular embodiments, $R^6$ and $R^7$ are independently ($C_3$-$C_6$ cycloalkyl)-($CH_2$).

In particular embodiments, $R^6$ and $R^7$ are independently ($C_3$-$C_6$ cycloalkyl)-($CH_2CH_2$).

In particular embodiments, $R^6$ and $R^7$ are independently V—($CH_2$)$_{0-1}$ wherein V is a 5-6 membered heteroaryl.

In particular embodiments, $R^6$ and $R^7$ are independently W—($CH_2$)$_{1-2}$ wherein W is phenyl optionally substituted with F, Cl, Br, I, OMe, $CF_3$ or Me. In a further embodiment, $R^6$ and $R^7$ are independently W—($CH_2$)$_{1-2}$ wherein W is phenyl optionally substituted with F, Cl, or Me.

In particular embodiments, $R^6$ and $R^7$ are independently $C_3$-$C_6$-cycloalkyl.

In particular embodiments, $R^6$ and $R^7$ are independently hydroxy-($C_3$-$C_6$-cycloalkyl).

In particular embodiments, $R^6$ and $R^7$ are independently fluoro-($C_3$-$C_6$-cycloalkyl).

In particular embodiments, $R^6$ and $R^7$ are independently $CH(CH_3)CH(OH)$phenyl.

In particular embodiments, $R^6$ and $R^7$ are independently 4-6 membered heterocycle optionally substituted with F, OH, cyclopropylmethyl, $C_1$-$C_3$ alkyl or $C(=O)(C_1$-$C_3$ alkyl).

In particular embodiments, $R^6$ and $R^7$ are independently $C_1$-$C_6$-alkyl optionally substituted with one or more groups independently selected from OH, O($C_1$-$C_6$-alkyl), CN, F, $NH_2$, NH($C_1$-$C_6$-alkyl), N($C_1$-$C_6$-alkyl)$_2$, tetrahydropyranyl, tetrahydrofuranyl, morpholinyl, oxetanyl, piperidinyl, and pyrrolidinyl. In a further embodiment, $R^6$ and $R^7$ are independently $C_1$-$C_6$-alkyl optionally substituted with one or more groups independently selected from OH, O($C_1$-$C_6$-alkyl), CN, F, $NH_2$, NH($C_1$-$C_6$-alkyl), N($C_1$-$C_6$-alkyl)$_2$, piperidinyl, and pyrrolidinyl.

In particular embodiments, $R^6$ and $R^7$ are independently $R^6$ and $R^7$ together with the nitrogen to which they are attached form a 4-6 membered heterocyclic ring optionally substituted with one or more groups independently selected from OH, halogen, oxo, $CF_3$, $CH_2CF_3$, and ($C_1$-$C_3$)alkyl.

In one embodiment of Formula I, m is 1, n is 0, p is 0, such that A is represented by the Formula 1:

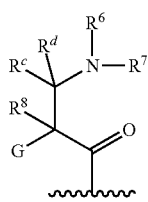

wherein G, $R^6$, $R^7$, $R^8$, $R^c$ and $R^d$ are as defined herein. In certain embodiments of group A, $R^8$ is H or OH. In certain embodiments, A has the following configuration:

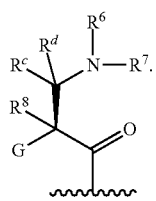

In certain embodiments of the A group having the Formula 1, $R^c$ and $R^d$ are H. In other embodiments, $R^c$ and $R^d$ together with the atom to which they are attached form a cyclopropyl ring.

In certain embodiments of the A group having the Formula 1, $R^6$ and $R^7$ are independently H, $C_3$-$C_6$-cycloalkyl, heteroaryl-($CH_2$), hydroxy-($C_3$-$C_6$-cycloalkyl), or ($C_{1-6}$)-alkyl optionally substituted with one or more groups independently selected from OH, OMe, and CN. In particular embodiments, $R^6$ and $R^7$ are independently H, methyl, ethyl, isopropyl, isobutyl, tert-butyl, 3-pentyl, CH(isopropyl)$_2$, $CH_2CH_2OH$, $CH_2CH_2CH_2OH$, $CH(CH_2CH_2OH)_2$, $CH_2CH_2OMe$, $CH(CH_2CH_2OMe)_2$, $CH_2CH_2CH_2OMe$, $CH_2CN$, $CH_2$-cyclopropyl, $CH_2$-cyclobutyl, $CH_2$-t-butyl cyclopentyl, cyclohexyl, $CH_2$-phenyl, $CH_2$-(pyrid-2-yl), $CH_2$-(pyrid-3-yl), $CH_2$-(pyrid-4-yl), 4-hydroxycyclohex-1-yl, or $CH(CH_3)CH(OH)$phenyl.

In particular embodiments of the A group having the Formula 1, $NR^6R^7$ is $NH_2$, NHMe, NHEt, NHPr, NHiPr, NHtBu, NH($CH_2$-cyclopropyl), NH($CH_2$-cyclobutyl), NH($CH_2$-tBu-tyl), NH(cyclopentyl), NH(cyclohexyl), NH(3-pentyl), NHCH(isopropyl)$_2$, NH($CH_2CH_2OH$), NH($CH_2CH_2CH_2OH$), NH($CH_2CH_2OMe$), NH($CH_2CH_2CH_2OMe$), NH($CH_2CN$), NMe$_2$, NMeEt, NMePr, NMe(iPr), NMe($CH_2$-cyclopropyl), NMe($CH_2$-cyclobutyl), NMe($CH_2CH_2OH$), NMe($CH_2CH_2CH_2OH$), NMe($CH_2CH_2OMe$), NMe($CH_2CH_2CH_2OMe$), NEt$_2$, NEtPr, NEt(iPr), NEt($CH_2$-cyclopropyl), NEt($CH_2$-cyclobutyl), NEt($CH_2CH_2OH$), NEt($CH_2CH_2CH_2OH$),

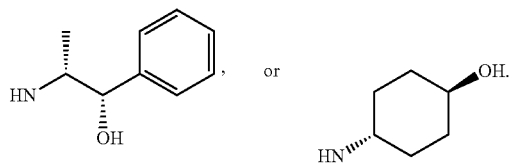

In other embodiments of the A group having the Formula 1, $R^6$ and $R^7$ together with the N to which they are attached form a 4-6 membered heterocyclic ring having a ring nitrogen atom and optionally having a second ring heteroatom selected form N and O, wherein said heterocyclic ring is optionally substituted with one or more groups independently selected from OH, F methyl, $CH_2CF_3$, and oxo. For example, in certain embodiments, $R^6$ and $R^7$ together with the N to which they are attached form a pyrrolidinyl, piperidinyl, azetidinyl, morpholinyl or piperizinyl ring, wherein said pyrrolidinyl, piperidinyl, azetidinyl, morpholinyl and piperazinyl rings are optionally substituted with one or more groups independently selected from OH, halogen, oxo, $CH_2CF_3$, and ($C_1$-$C_3$)alkyl. In particular embodiments of the A group having the Formula 1, $NR^6R^7$ is selected from the structures:

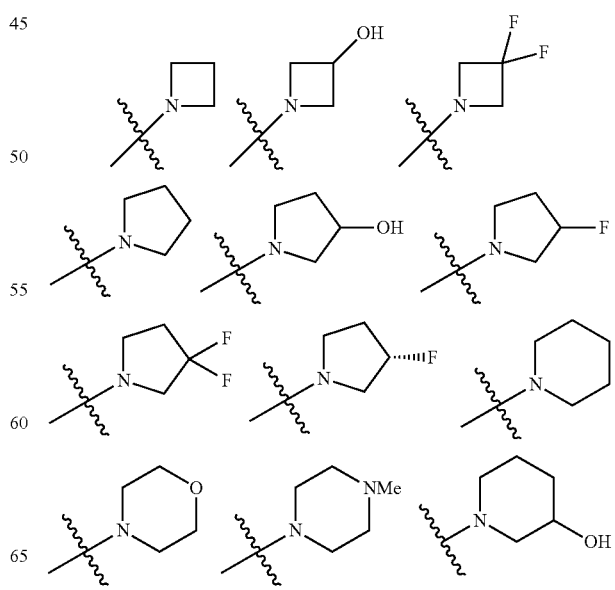

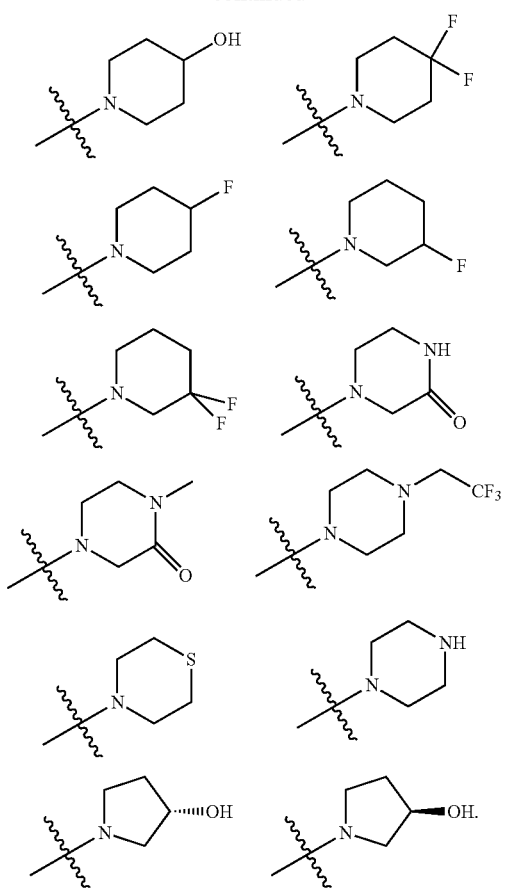

In certain embodiments of the group A having the Formula 1, $R^6$ and $R^8$ together with the atoms to which they are attached form a 5-6 membered heterocyclic ring having one or two ring nitrogen atoms. In other embodiments, $R^6$ and $R^8$ together with the atoms to which they are attached form a pyrrolidinyl or piperidinyl ring.

In particular embodiments, the A group having the Formula 1 is selected from the formulas:

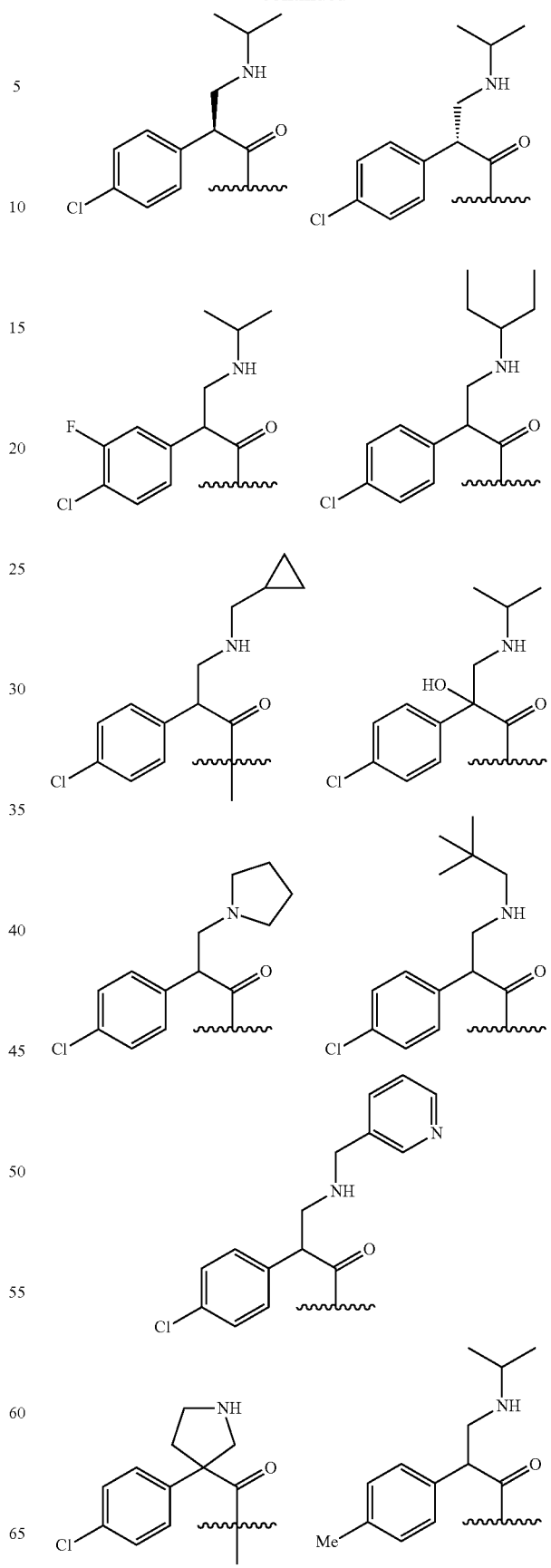

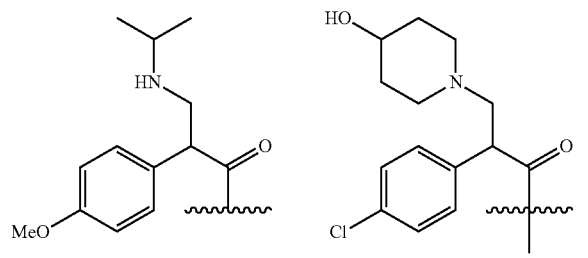
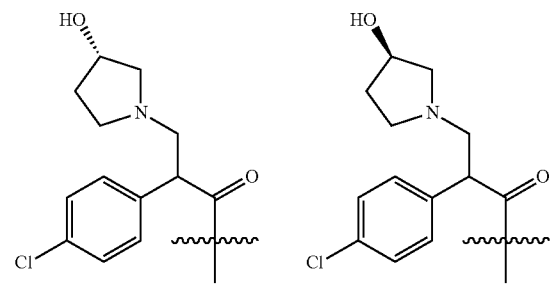
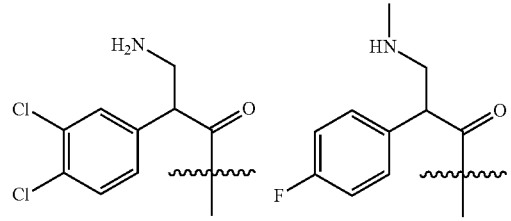
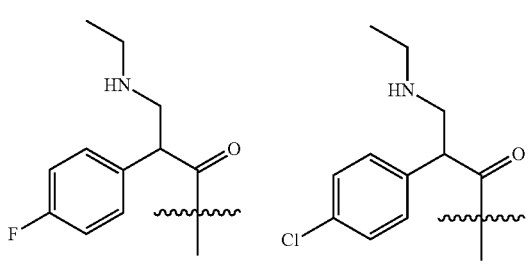
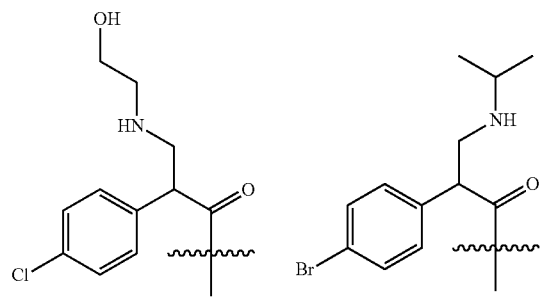
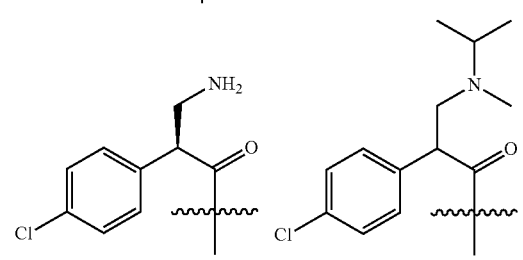
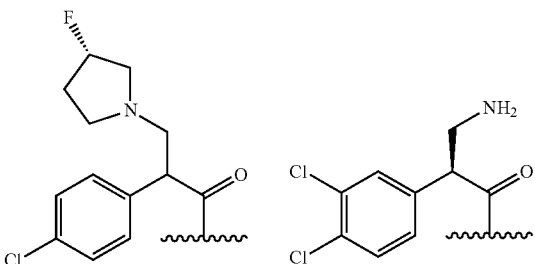
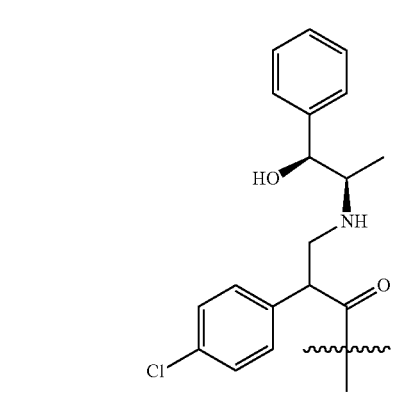
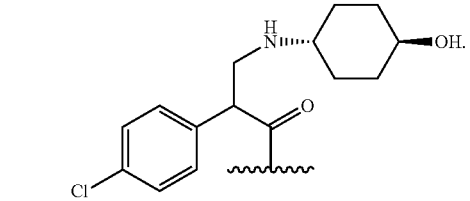
In certain embodiments, compounds of the present invention are represented by Formula 1B:
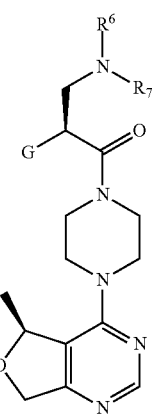
1B
wherein G, $R^6$ and $R^7$ are as defined herein.
In another embodiment of Formula I, m is 1, n is 1 and p is 0, such that A is represented by the Formula 2:

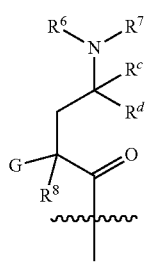

wherein G, $R^6$, $R^7$, $R^8$, $R^c$ and $R^d$ are as defined herein. In certain embodiments, the A group has the following configuration:

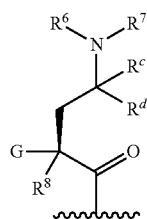

In certain embodiments of the group A having the Formula 2, $R^8$ is H.

In certain embodiments of the group A having the Formula 2, $R^c$ and $R^d$ are H. In other embodiments, $R^c$ and $R^d$ are methyl. In other embodiments, $R^c$ and $R^d$ together with the atom to which they are attached form a cyclopropyl ring.

In certain embodiments of the group A having the Formula 2, $R^6$ and $R^7$ are independently H, methyl, ethyl, propyl, isopropyl, $CH_2$-cyclopropyl, or $CH_2$-cyclobutyl. In certain embodiments, $NR^6R^7$ of Formula 2 is $NH_2$, $NHCH_3$, NHEt, NHPr, NH(iPr), NH($CH_2$-cyclopropyl), NH($CH_2$-cyclobutyl), $NMe_2$, NMeEt, NMePr, NMe(iPr), $NEt_2$, NEtPr, or NEt(iPr). In particular embodiment, $NR^6R^7$ is $NH_2$.

In certain embodiments of the group A having the Formula 2, $R^6$ and $R^7$ together with N form a 5-6 membered heterocyclic ring having a ring nitrogen atom and optionally having an additional ring nitrogen atom. For example, in certain embodiments, $R^6$ and $R^7$ together with N form a heterocyclic ring selected from the structures:

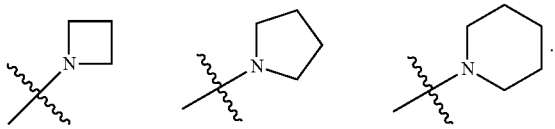

In other embodiments, $R^6$ and $R^8$ together with the atoms to which they are attached form a piperidinyl or pyrrolidinyl ring.

Exemplary embodiments of group A of Formula 2 include the structures:

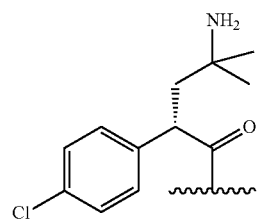

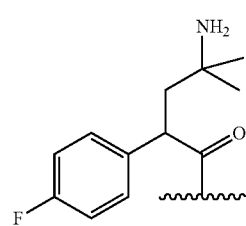

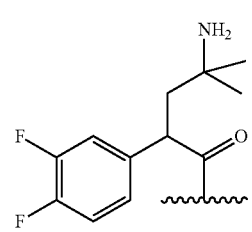

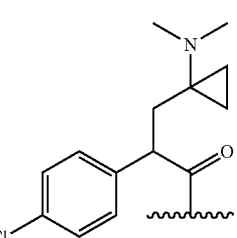

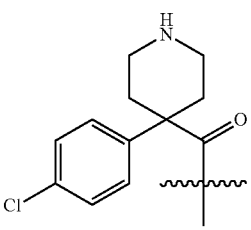

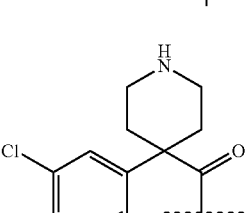

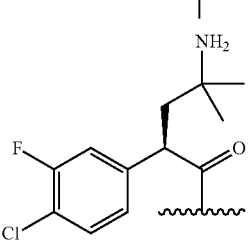

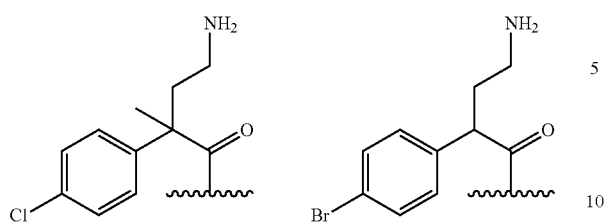

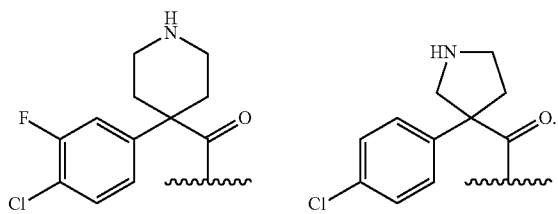

In certain embodiments, compounds of the present invention are represented by Formula 2B:

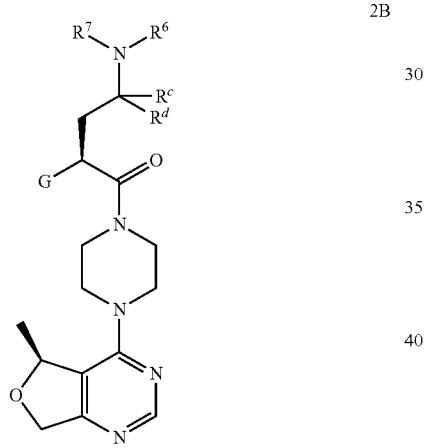

wherein G, $R^c$, $R^d$, $R^6$ and $R^7$ are as defined herein.

In other embodiments of Formula I, m is 1, n is 0 and p is 1, such that A is represented by the Formula 3:

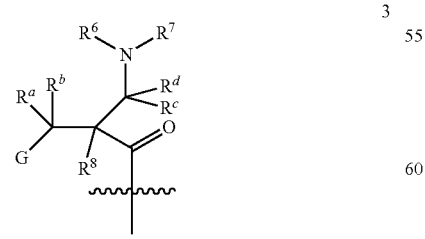

wherein G, $R^6$, $R^7$, $R^8$, $R^a$, $R^b$, $R^c$ and $R^d$ are as defined herein. In certain embodiments, group A has the configuration:

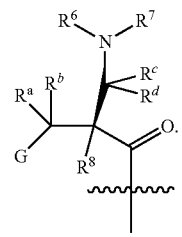

In certain embodiments of the group A of Formula 3, $R^8$ is H.

In certain embodiments of the group A of Formula 3, $R^c$ and $R^d$ together with the atom to which they are attached form a cyclopropyl ring.

In certain embodiments of the group A of Formula 3, $R^6$ and $R^7$ are independently H, methyl, ethyl, propyl, isopropyl, t-butyl, $CH_2$-cyclopropyl, or $CH_2$-cyclobutyl. In certain embodiments, $NR^6R^7$ of Formula 3 is $NH_2$, NHMe, NHEt, NHPr, NH(iPr), NHtBu, NH($CH_2$-cyclopropyl), or NH($CH_2$-cyclobutyl).

In other embodiments of group A of Formula 3, $R^a$ and $R^8$ are H, and $R^b$ and $R^6$ together with the atoms to which they are attached form a 5 to 6 membered heterocyclic ring wherein one of the ring atoms is nitrogen. In certain embodiments, $R^b$ and $R^6$ together with the atoms to which they are attached form a pyrrolidinyl ring. In certain embodiments, $R^7$ is H.

In particular embodiments, group A of Formula 3 is selected from the structures:

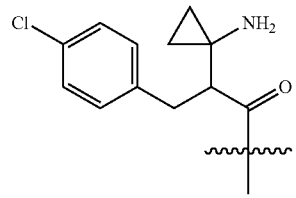

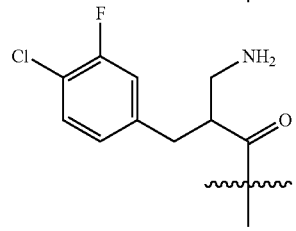

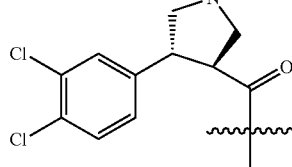

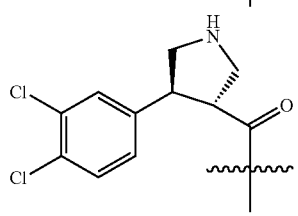

-continued

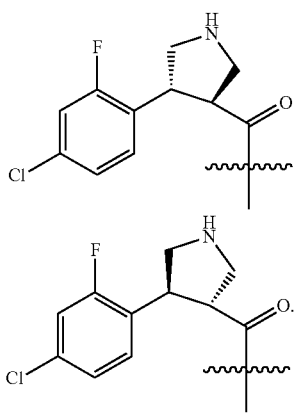

In certain embodiments, compounds of the present invention are represented by Formula 3B:

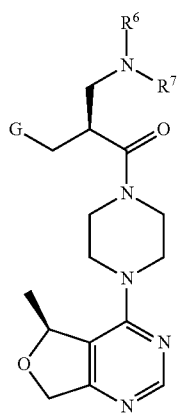

3B wherein G, $R^6$ and $R^7$ are as defined herein.

In other embodiments of Formula I, m is 0, n is 0 and p is 1, such that A is represented by the formula:

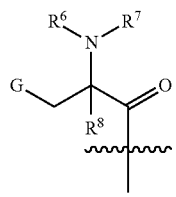

4 wherein G, $R^6$, $R^7$, and $R^8$ are as defined herein. In certain embodiments, A has the following configuration:

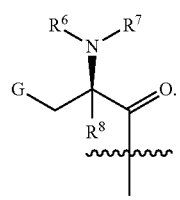

In certain embodiments of the group A of Formula 4, $R^8$ is H.

In certain embodiments of the group A of Formula 4, $R^6$ and $R^7$ are independently H or Me.

In particular embodiments, A is selected from the structures:

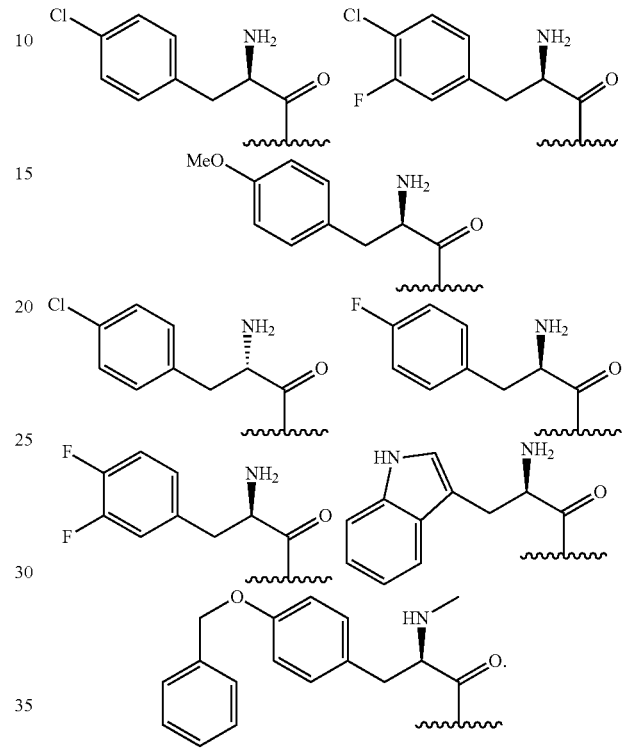

In certain embodiments, compounds of the present invention are represented by Formula 4B:

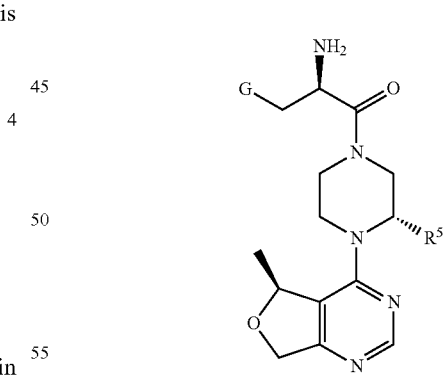

4B wherein G and $R^5$ are as defined herein.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g., melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula I include solvates, pharmaceutically acceptable prodrugs and salts (including pharmaceutically acceptable salts) of such compounds.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" can also be used to refer to a complex wherein the solvent molecule is water.

A "prodrug" is a compound that may be converted under physiological conditions or by solvolysis to the specified compound or to a salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., 1996, 39, 10. More specific examples include replacement of the hydrogen atom of the alcohol group with a group such as $(C_1-C_6)$alkanoyloxymethyl, $1-((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —P(O)(O$(C_1-C_6)$alkyl$)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, or —C(Y$_2$)Y$_3$ wherein Y$_2$ is H or methyl and Y$_3$ is mono-N— or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

Alternatively or additionally, compound of the invention may possess a sufficiently acidic group, a sufficiently basic group, or both functional groups, and accordingly react with any of a number of inorganic or organic bases or acids to form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labelled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result, for example, from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolites are identified, for example, by preparing a radiolabelled (e.g., $^{14}$C or $^3$H) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Synthesis of Compounds of Formula I

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or pharmaceutically acceptable salts thereof.

For illustrative purposes; Scheme 1 and Schemes A-K show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by Scheme 1

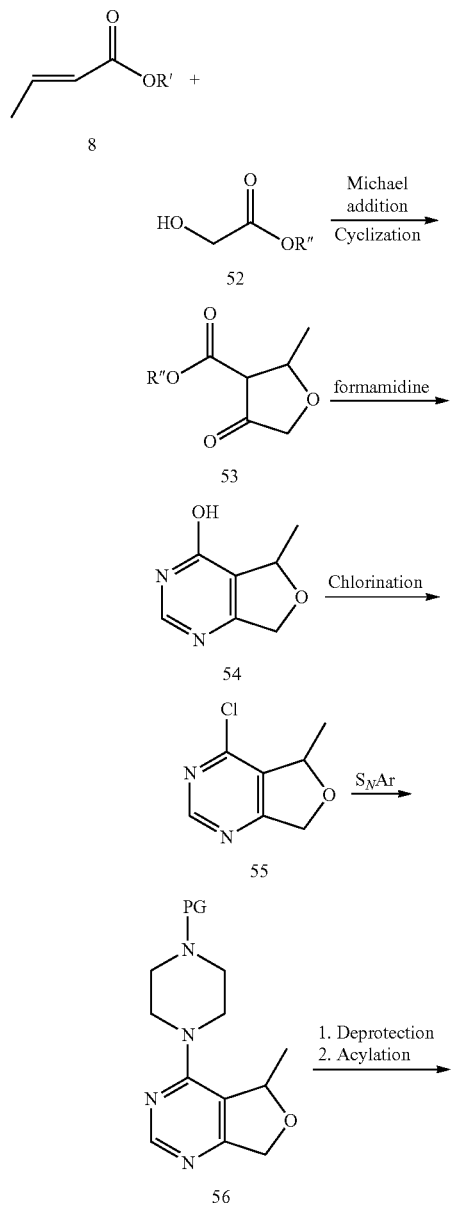

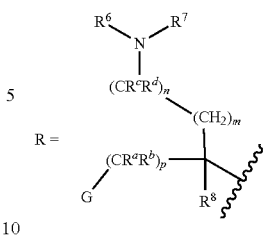

Scheme 1 shows a method of preparing compound 57 of Formula I wherein $R^1$ is Me. The ketoester 53 can be prepared in one step using the hydroxy ester compound 52 and the unsaturated ester 8 under basic conditions (eg. NaH) at temperatures ranging from −20° C. to 100° C. Formation of the pyrimidine compound 54 is executed by heating (e.g. 40° C. to reflux) the ketoester 53 with (for example) formamidine acetate in a solvent such as toluene or benzene. Compound 54 can be further advanced by activation of the pyrimidin-4-ol to any appropriate leaving group: For example, compound 55 can be prepared using any number of alternative methods (e.g., $POCl_3$ in dichloroethane at reflux, etc.) A subsequent $S_NAr$ reaction between 55 and an appropriately substituted piperazine (for example, N-Boc piperazine) in a suitable solvent (for example, NMP) in the presence of a base (such as $NEt_3$ or DIPEA) at an appropriate temperature (e.g., room temperature to reflux) provides access to compound 56. In certain cases, with poorer leaving groups, or more hindered reagents, alternative conditions may be required, such as the use of sealed tube apparatus or microwave chemistry. Subsequent protecting group (PG) removal (e.g., 4N HCl in dioxane mediated removal of the Boc group; or see, 'Protective Groups in Organic Synthesis' by Greene and Wuts, Wiley-Interscience, third edition, Chapter 7) followed by acylation with a suitable acid chloride in the presence of base (e.g., $NEt_3$, DIPEA, or DBU, etc.) or the coupling of an acid using an appropriate coupling reagent (EDCI, CDI or HATU, etc.) in the presence of base (e.g., $NEt_3$, DIPEA or DBU, etc.) provides compound 57. Any protecting group contained within this acid unit may then be removed under standard conditions (see, for example, 'Protective Groups in Organic Synthesis' by Greene and Wuts, Wiley-Interscience, third edition.)

Accordingly, another aspect of the invention provides a method of preparing compounds of Formula I, comprising:

reacting a compound having the formula:

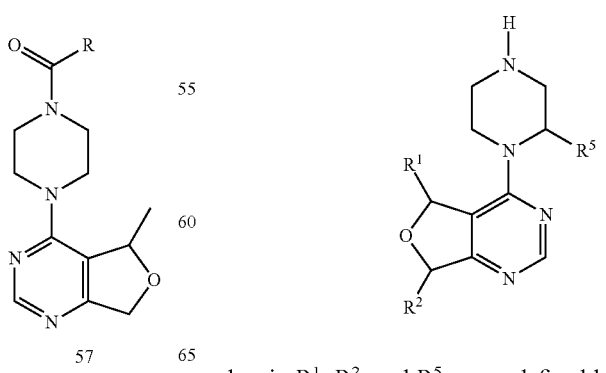

wherein $R^1$, $R^2$, and $R^5$ are as defined herein, with a compound having the formula:

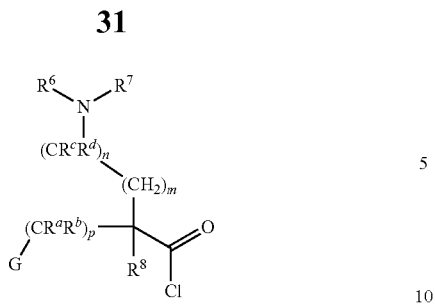

wherein $R^6$, $R^7$, $R^8$, $R^a$, $R^b$, $R^c$, $R^d$, G, n, m and p are as defined herein.

The amino acids used in the synthesis of compounds of Formula I as illustrated in Scheme 1 are either commercially available or may be prepared according to the methods disclosed herein. For example, in certain embodiments the amino acids used to prepare compounds of Formula I include β-phenylglycine amino acids having the Formula 1A, γ-phenylglycine amino acids having the Formula 2A, β-phenylalanine amino acids having the Formula 3A, and γ-phenylalanine amino acids having the Formula 4A.

2A

3A

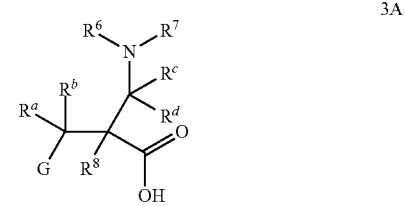

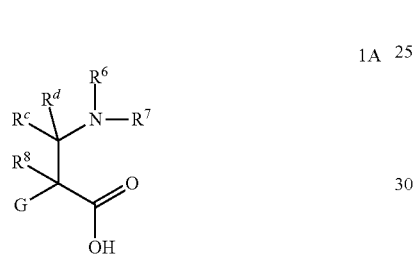

1A

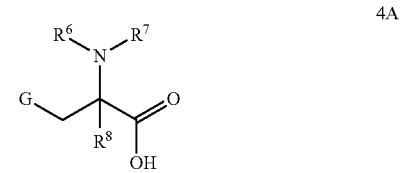

4A

Methods of preparing amino acids of Formulas 1A-4A are shown in Schemes A-K.

Scheme A

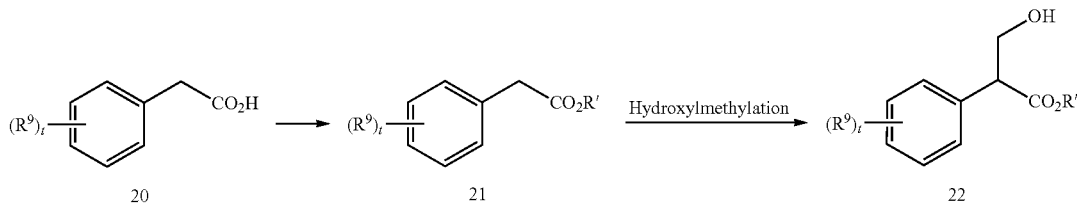

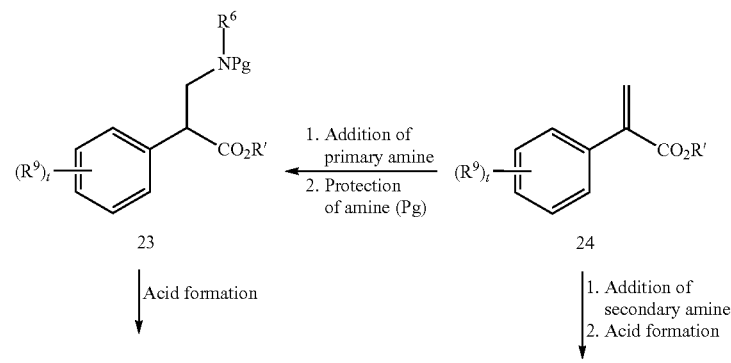

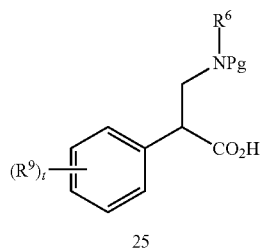

25

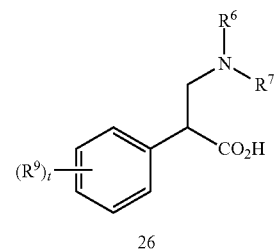

26

Scheme A illustrates a method of preparing optionally substituted β-phenylglycine amino acids 25 and 26 of the Formula 1 wherein $R^8$ is H, $R^c$ and $R^d$ are H, and $R^6$, $R^9$ and t are as defined herein and $R^7$ is H or an amine protecting group. According to Scheme A, the acid 20 is converted to an ester 21 wherein R' is alkyl using standard conditions such as treatment with an appropriate alcohol (e.g. MeOH) in the presence of a catalytic amount of an acid such as concentrated $H_2SO_4$ or a coupling agent such as DCC/DMAP; or alternatively by treatment with an appropriate electrophile (e.g., MeI, EtBr, BnBr) in the presence of a base such as $NEt_3$/DMAP at an appropriate temperature (e.g., $-20°$ C. to $100°$ C.). The appropriate choice of ester is determined by the conditions required to reform the acid at the end of the synthesis, with many appropriate examples and conditions being listed in 'Protective Groups in Organic Synthesis' by Greene and Wuts, Wiley-Interscience, third edition, Chapter 5. Introduction of the hydroxymethyl group to provide compound 22 may be performed by treatment with an appropriate aldehyde (e.g., formaldehyde) in the presence of base such as NaOEt at an appropriate temperature (e.g., $-20°$ C. to room temperature). Activation of the alcohol group of compound 22 to form a leaving group (e.g., a mesylate, tosylate, halide) may be accomplished by treatment with, for example, methanesulphonyl chloride in the presence of excess base such as $NEt_3$, DIPEA, or DBU at an appropriate temperature (e.g., $-20°$ C. to room temperature). In many cases the olefin 24 can be isolated directly from this procedure, in other cases warming ($30°$ C. to $100°$ C.) or additional base (e.g. DBU in the case of halide) may be required to complete the elimination to provide compound 24. The activated olefin 24 may be treated with the desired primary amine (e.g., ethylamine) in a suitable solvent, such as THF, at an appropriate temperature (e.g., $-20°$ C. to reflux) to generate the aminoester intermediate. In the case wherein compound 24 has an electron rich aromatic ring or electron poor/bulky primary amine, heating (e.g. $30$-$240°$ C. in a sealed tube) or microwave chemistry may be required. Protection of the amine group (for example as Boc-group) may be accomplished using $Boc_2O$ under standard conditions to provide compound 23 wherein Pg is a protecting group. Alternative protecting groups may be used, and many appropriate examples are listed in 'Protective Groups in Organic Synthesis' by Greene and Wuts, Wiley-Interscience, third edition, Chapter 7. Saponification of the ester 23 to form the protected amino acid 25 may be accomplished using conditions appropriate for the ester (e.g., aqueous LiOH for methyl esters, hydrogenation for benzyl esters, acid for t-butyl esters).

Alternatively, the activated olefin 24 may be treated with a secondary amine (e.g., diethylamine) in a suitable solvent such as THF at an appropriate temperature (e.g., $-20°$ C. to reflux) to generate the aminoester intermediate (not shown). In the case wherein compound 24 has an electron rich aromatic ring or electron poor/bulky secondary amine, heating (e.g., $30$-$240°$ C. in a sealed tube) or microwave chemistry may be required. Saponification of the ester to form the amino acid 26 may be accomplished using conditions appropriate for the ester (e.g., aqueous LiOH for methyl esters, hydrogenation for benzyl esters, acid for t-butyl esters, etc.).

Scheme B

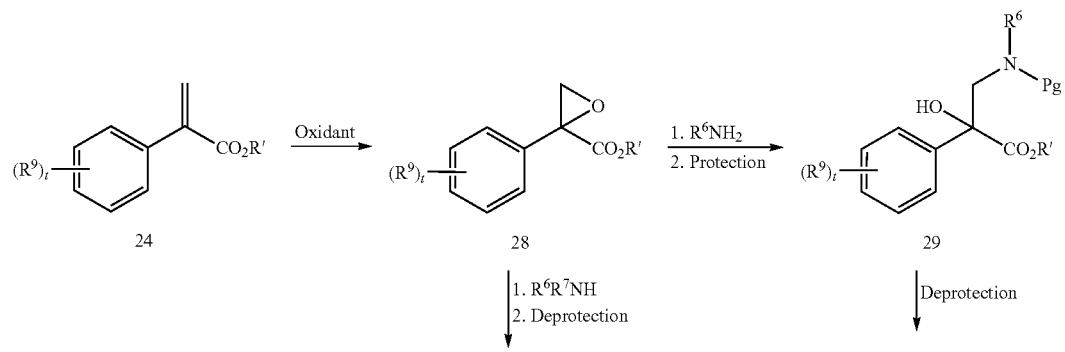

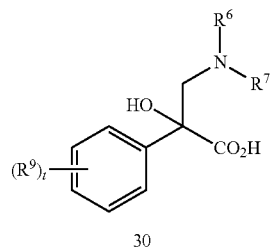

30

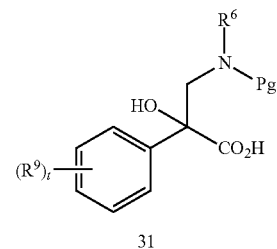

31

Scheme B shows a method of preparing optionally substituted β-phenylglycine amino acids 30 and 31 of Formula 1 wherein $R^8$ is OH, $R^c$ and $R^d$ are H, and $R^6$, $R^9$ and t are as defined herein and $R^7$ is as defined herein or an amine protecting group. Oxidation of the unsaturated ester 24 (prepared according to Scheme A), wherein t is 0-4 and R' is alkyl, using a standard oxidizing agent such as MCPBA at an appropriate temperature (room temperature to reflux) provides the epoxide intermediate 28. Intermediate 28 may be treated with an appropriate amine, typically at high temperature (e.g., 50-300° C.) and high pressure (e.g., in a sealed tube or a bomb) to give the amino alcohol 29 or 30. If a secondary amine is used (such as in the preparation of compound 30), then deprotection of the ester using conditions listed in 'Protective Groups in Organic Synthesis' by Greene and Wuts, Wiley-Interscience, third edition, Chapter 5 may be used (e.g., LiOH for a methyl ester, hydrogenation for a benzyl ester, etc). When a primary amine is used (such as in the preparation of compound 29), protection of the amine (e.g., as a Boc-group using Boc anhydride) followed by deprotection of the ester (using the above conditions) provide the hydroxylated amino acid 31.

Scheme C shows a method of preparing optionally substituted β-phenylglycine amino acids 36 of the Formula 1 wherein $R^8$ is methyl, $R^6$ is H, $R^7$ is an amine protecting group, and $R^9$ and t are as defined herein. The ester 32, wherein R''' is alkyl, can be treated with a base (e.g. NaOtBu) at an appropriate temperature (e.g., 0° C. to reflux) to form the anion, followed by addition of an electrophile (e.g., tert-butyl 2-bromoacetate) at an appropriate temperature (e.g., 78° C. to room temperature) to give the homologated ester 33. Saponification of the t-butyl ester of compound 33 using an appropriate acid such as TFA or HCl at an appropriate temperature (e.g., 0° C. to reflux) provides compound 34. A Curtius rearrangement of compound 34 using, for example, DPPA in the presence of mild base such as $NEt_3$ at an appropriate temperature (e.g., 0° C. to reflux), followed by treatment of the reactive intermediate with an alcohol (e.g. tBuOH), optionally in the presence of a Lewis acid (e.g. $SnCl_2$) at higher temperature (e.g., 40-200° C.) provides compound 35 wherein Pg is an amine protecting group. The choice of alcohol used to prepare compound 35 determines the amine protecting group (e.g. tBuOH provides the Boc-amine). Deprotection of the ester group of compound 35 using standard conditions (e.g., with LiOH when the protecting group is a methyl ester, hydrogenation for a benzyl ester, etc.) gives the acid compound 36.

Scheme C

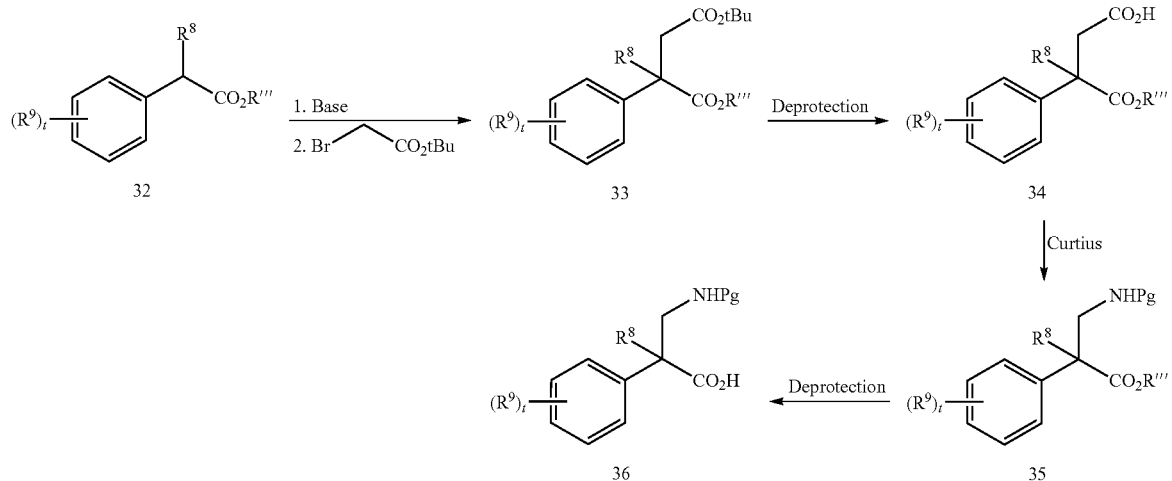

Scheme D

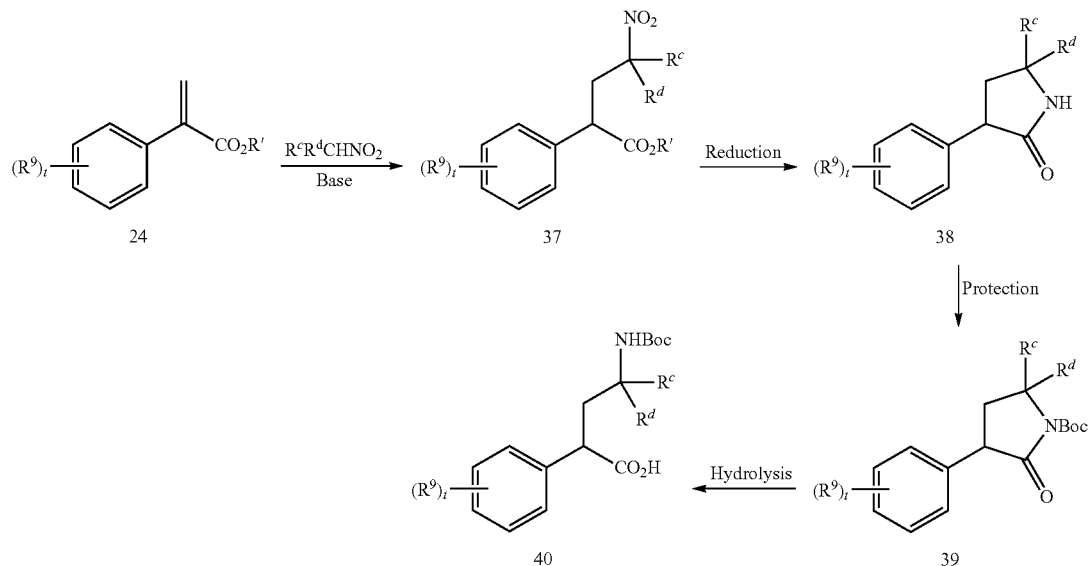

Scheme D shows a method of preparing optionally substituted γ-phenylglycine amino acids 40 of Formula 2 wherein $R^c$, $R^d$, $R^9$ and t are as defined herein, $R^6$ is H, and $R^7$ is an amine protecting group such as Boc. The starting unsaturated ester 24, prepared according to Scheme A, can be treated with a substituted nitromethane derivative (e.g. nitroethane) in the presence of a base such as DBU at an appropriate temperature (e.g., 0° C. to room temperature) to give the homologated adduct 37. The nitro group of compound 37 can be reduced using standard conditions (e.g., hydrogenation, Zn/acid, etc.) at an appropriate temperature (e.g., room temperature to reflux), and the resulting intermediate can be cyclized to give the lactam intermediate 38. Protection of the amine, for example with a Boc-group to provide compound 39, may be accomplished using $Boc_2O$ under standard conditions. Alternative protecting groups may be used, and many appropriate examples are listed in 'Protective Groups in Organic Synthesis' by Greene and Wuts, Wiley-Interscience, third edition, Chapter 7. Treatment of compound 39 with an aqueous base such as LiOH or KOH at an appropriate temperature (e.g., 0 to 100° C.) effects ring opening of the lactam to give the appropriately substituted, protected amino acid compound 40.

Scheme E

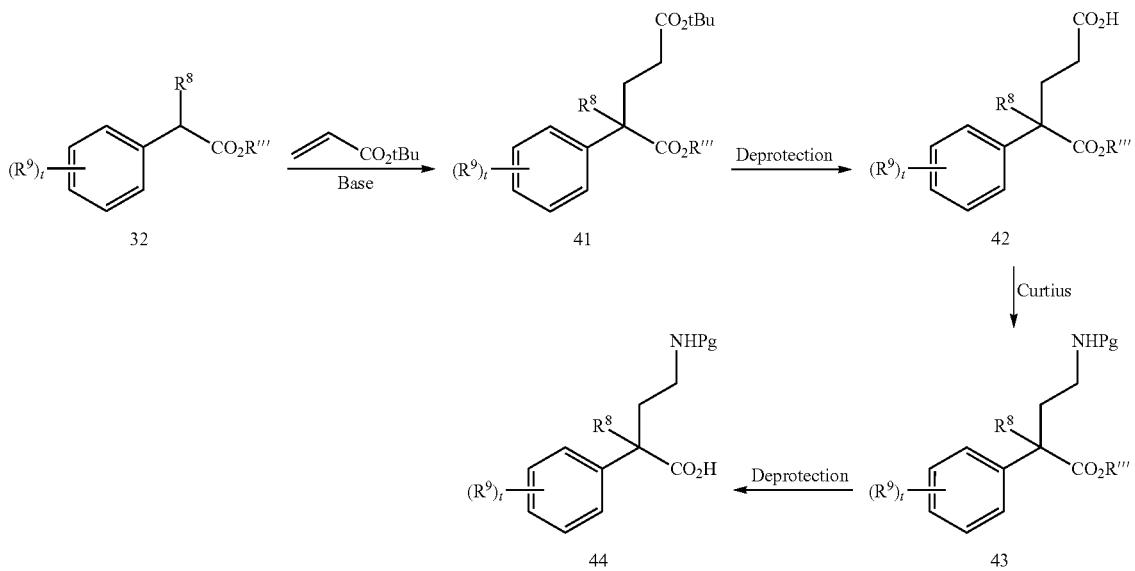

Scheme E shows a method of making optionally substituted γ-phenylglycine amino acids 44 of Formula 2 wherein $R^8$ is methyl, $R^6$ is H, $R^7$ is an amine protecting group, and $R^9$ and t are defined herein. The ester 32, wherein R''' is alkyl and t is 0-4, can be treated with a suitable base such as KOtBu at an appropriate temperature (e.g., 0° C. to reflux) to form the anion, followed by addition of an acrylate unit (e.g., t-butylacrylate) at a temperature ranging from −78° C. to room temperature to give the homologated ester 41. Saponification of the t-butyl ester of compound 41 by treatment with a suitable acid such as TFA or HCl at an appropriate temperature (e.g., 0° C. to reflux) provides compound 42. A Curtius rearrangement of compound 42 using, for example, DPPA in the presence of mild base such as $NEt_3$ at an appropriate temperature (e.g., 0° C. to reflux), followed by treatment of the reactive intermediate with an appropriate alcohol (e.g. t-BuOH), optionally in the presence of a Lewis acid (e.g. $SnCl_2$) at elevated temperatures (e.g. 40-200° C.) provides compound 43. The choice of alcohol determines the amine protecting group of compound 43 (e.g., t-BuOH provides the Boc-amine). Deprotection of the ester of compound 43 under standard conditions (e.g., LiOH for a methyl ester, hydrogenation for a benzyl ester, etc.) gives the acid 44.

In an alternative to Scheme E, $R^8$ may be hydrogen.

2-cyanoacetate) in the presence of a suitable base such as piperidine at an appropriate temperature (e.g., room temperature to reflux) to give the unsaturated ester 46. Reduction of the olefin and the nitrile groups of compound 46 to provide compound 47 may be accomplished in a number of ways. For example, the olefin may be reduced with any agent known to effect 1,4-reductions, such as $NaBH_4$. The nitrile may be reduced using agents such as $LiAlH_4$ or $NaBH_4$ in the presence of a Lewis acid such as $BF_3OEt_2$ or TFA. A number of alternative reducing agents may be used, such as those listed in 'Reductions in Organic Chemistry' by Hudlicky, ACS monograph, $2^{nd}$ edition, Chapter 18. If desired, the primary amine 47 can be monoalkylated or bisalkylated at this stage using standard conditions (e.g., reductive amination using an appropriate aldehyde, Lewis acid and reducing agent) to provide intermediates (not shown) en route to compounds 48 and 49. To prepare primary and secondary amines, protection may be accomplished using any number of protecting groups (e.g. 'Protective Groups in Organic Synthesis' by Greene and Wuts, Wiley-Interscience, third edition, Chapter 7), for

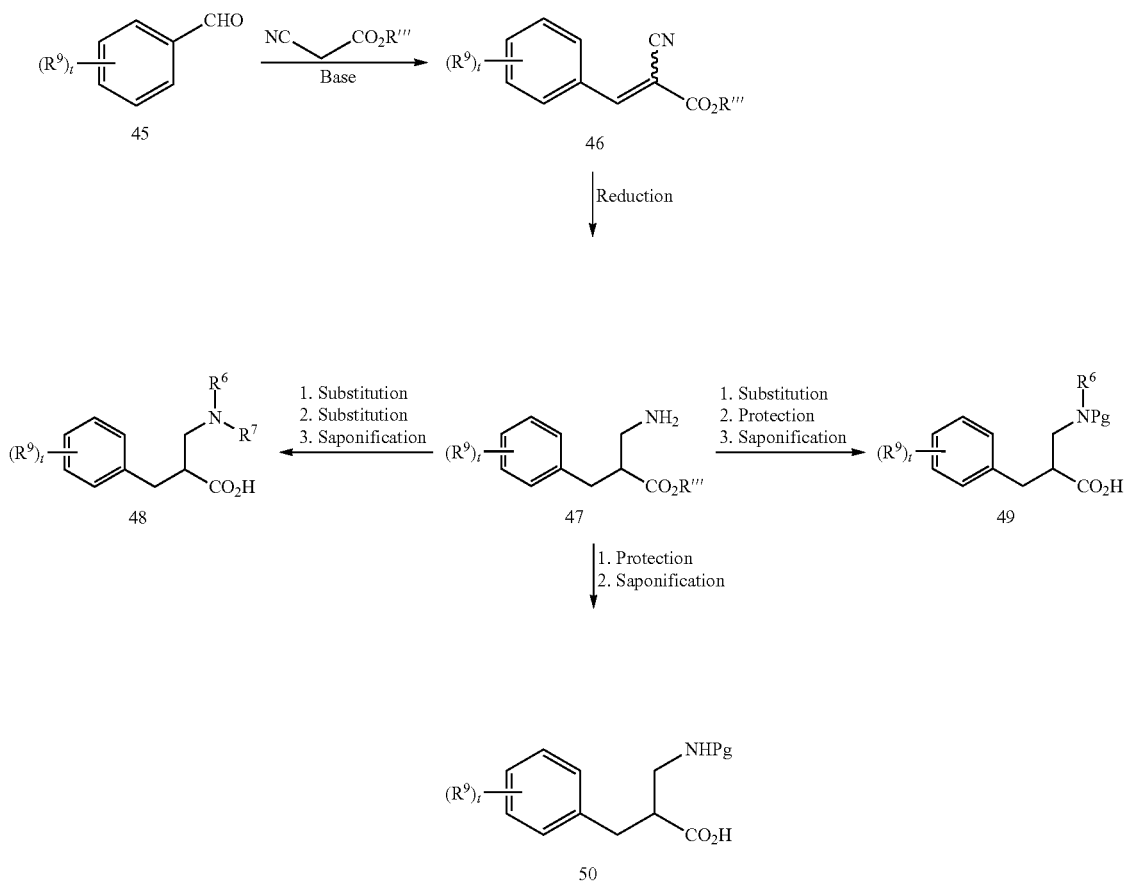

Scheme F

Scheme F shows a method of preparing optionally substituted β-phenylalanine amino acids 48, 49 and 50 of Formula 3 wherein $R^6$ is H, $R^7$ is an amine protecting group, $R^c$ and $R^d$ are H, and $R^9$ and t are as defined herein. An appropriately substituted aldehyde 45 can be treated with a cyanoacetate of the formula $CN$—$CH_2CO_2R'''$ wherein $R'''$ is alkyl (e.g., ethyl example as a Boc-group using Boc anhydride at 0° C. to room temperature. Cleavage of the ester group to form the amino acid 48, 49 or 50 may be accomplished using an aqueous bases such as LiOH or KOH, or any of the alternative reagents listed in the aforementioned 'Protecting Groups' text (e.g., hydrogenation for a benzyl ester).

Scheme G

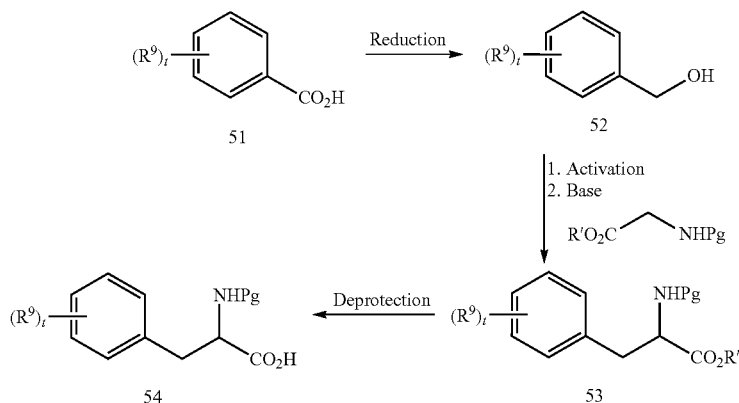

Scheme G shows a method of preparing optionally substituted α-phenylalanine amino acids 54 of Formula 4 wherein $R^6$ is H, $R^7$ is an amine protecting group, and $R^9$ and t are as defined herein. An appropriately substituted acid 51 may be reduced to the benzyl alcohol 52 using for example $LiAlH_4$ at a temperature ranging from room temperature to reflux. The alcohol group of compound 52 can be activated as a leaving group (e.g. halide, mesylate, etc.) using, for example, $PBr_3$, $MsCl/NEt_3$, etc. Displacement of this leaving group using a protected glycine derivative such as ethyl 2-(diphenylmethyleneamino)acetate in the presence of strong base such as LDA, n-BuLi provides the amino ester intermediate 53 wherein $R^1$ is alkyl and Pg is a protecting group. Appropriate protecting groups are listed in 'Protective Groups in Organic Synthesis' by Greene and Wuts, Wiley-Interscience). The amine protecting group may be changed at this stage, for example to introduce a Boc-group. Subsequent deprotection of the ester 53 (e.g., using 3N HCl, LiOH, hydrogenation for a benzyl ester, etc.) at an appropriate temperature (e.g., 0° C. to reflux) provides the desired N-protected amino acid 54.

Scheme H shows a method of preparing optionally substituted γ-phenylglycine amino acids 56 of Formula 2 wherein $R^6$ and $R^8$ together with the atoms to which they are attached form a spirocyclic heterocyclic ring, $R^7$ is an amine protecting group, and $R^9$ and t are as defined herein. According to Scheme H, the unsaturated ester 24 can be treated with a suitably protected glycine derivative (e.g., benzylglycine) and formaldehyde under dry conditions (e.g., with addition of molecular sieves) at an appropriate temperature (e.g., room temperature to reflux) to generate compound 55. Cleavage of the benzyl group using standard conditions (e.g., via hydrogenation, 1-chloroethylformate, etc.) followed by addition of an amine protecting group such as a Boc-group and cleavage of the ester under standard conditions (e.g. LiOH for a methyl ester, acid for a t-butyl ester, etc., at 0° C. to reflux) provides the N-protected amino acid 56.

Scheme H

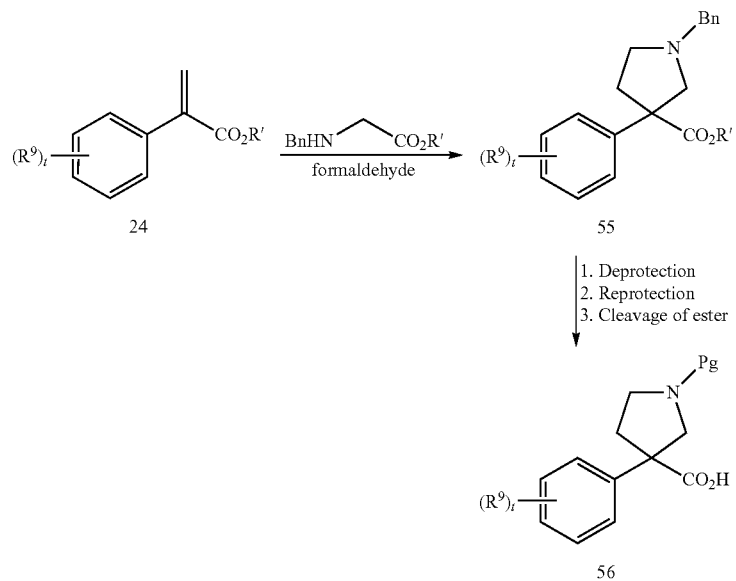

Scheme I

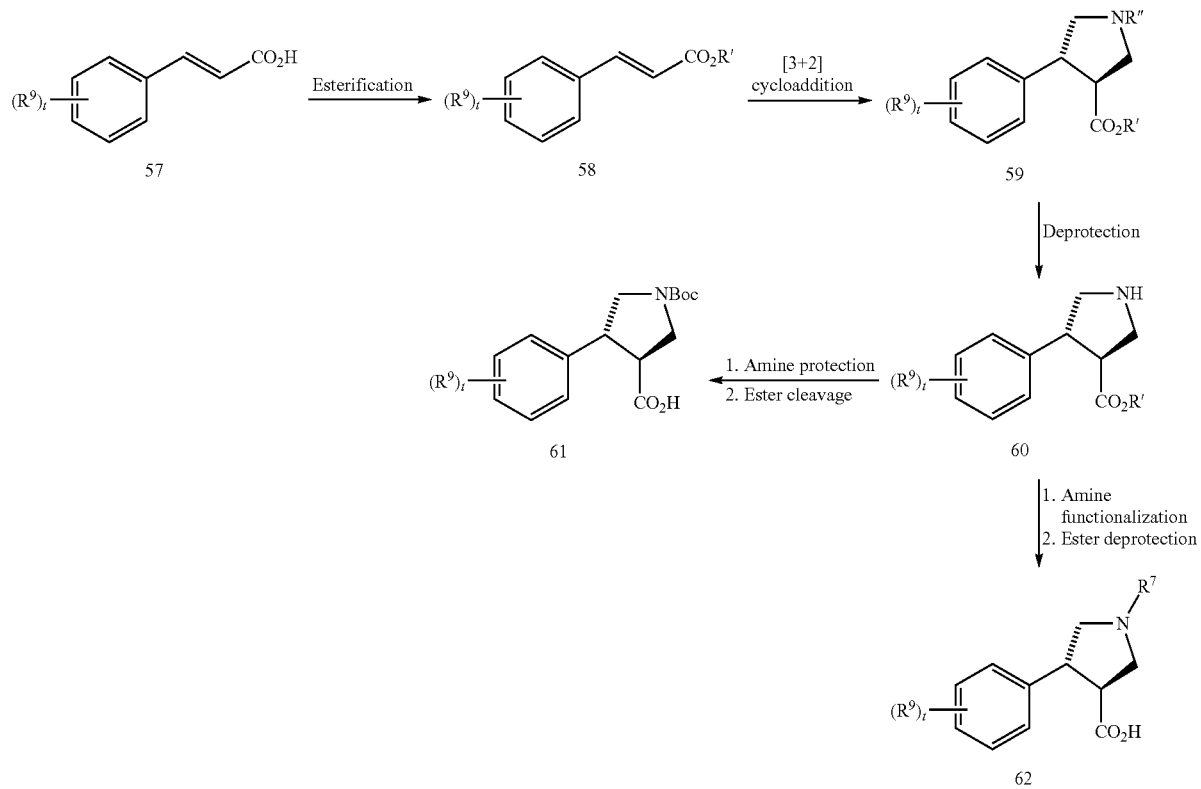

Scheme I shows a method of preparing optionally substituted β-phenylalanine amino acids 61 and 62 of Formula 3 wherein $R^c$ and $R^d$ are H, $R^6$ and $R^b$ together with the atoms to which they are attached form a heterocyclic ring, and $R^7$, $R^9$ and t are as defined herein. The acid 57 is converted to an ester 58 using standard conditions such as treatment with an appropriate alcohol (e.g., MeOH) in the presence of either catalytic acid (e.g. concentrated $H_2SO_4$ or TMSCl) or a coupling agent (e.g. DCC/DMAP); or alternatively by treatment with an appropriate electrophile (e.g. MeI, EtBr, BnBr) in the presence of a suitable base such as $NEt_3$/DMAP at appropriate temperatures (e.g., −20° C. to 100° C.). The appropriate choice of ester is determined by the conditions required to reform the acid at the end of the synthesis, such as described in 'Protective Groups in Organic Synthesis' by Greene and Wuts, Wiley-Interscience, third edition, Chapter 5. Cyclization of compound 58 to provide compound 59 may be achieved using, for example, N-(methoxymethyl)(phenyl)-N-((trimethylsilyl)methyl)methanamine in the presence of TFA. This particular set of reagents generates the benzylamine, which can be cleaved to provide compound 60 under standard conditions such as such as hydrogenation at −20° C. to 50° C. or any other standard conditions such as those listed in 'Protective Groups in Organic Synthesis' by Greene and Wuts, Wiley-Interscience, third edition, Chapter 7. Protection of the free amine of compound 60 with an alternative protecting group (e.g., Boc) using reagents listed in the aforementioned text, such as Boc-anhydride, followed by cleavage of the ester using standard conditions appropriate for the ester (e.g. aqueous LiOH for methyl esters, hydrogenation for benzyl esters, acid for t-butyl esters) provides the acid compound 61. Alternatively, the free amine can be functionalized further (e.g. using alkylation, reductive amination, or acylation conditions), followed by ester cleavage to generate the tertiary amino acid compound 62.

Scheme J

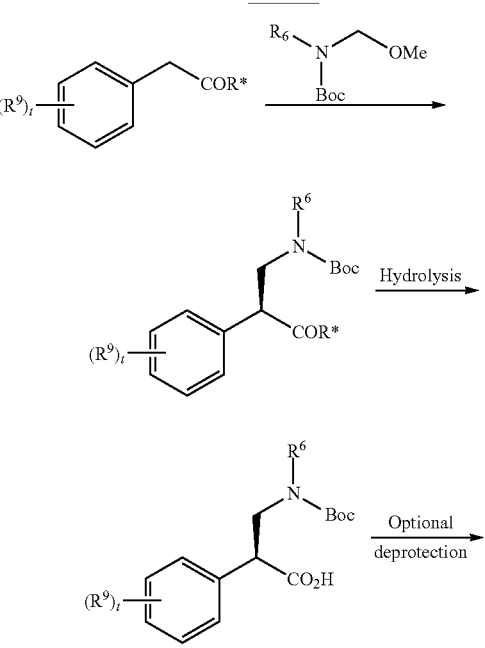

-continued

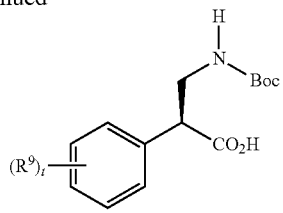

Either enantiomer of the beta-amino acids may be prepared using a procedure such as that shown in Scheme J. A 2-phenylacetate coupled with an appropriate chiral auxiliary (R*) (for example, an Evans' auxiliary or a Sultam) with the appropriate stereochemistry to generate the desired chemistry at the beta-position of the amino acid may be treated with an imine or iminium ion synthon (e.g. prepared in situ by the presence of a Lewis acid (e.g. $TiCl_4$) and an appropriately substituted alkoxymethanamine or N-(alkoxymethyl)amide/carbamate at −100° C. to 50° C.). The asymmetric addition may require the presence of Lewis acids (e.g. $TiCl_4$), amine bases (e.g. Hunig's base) and lower temperatures (e.g. −100° C. to 0° C.) to generate the best levels of stereochemical induction. If the diastereoselectivity is lower than required, the separate diastereomers may be separated at this stage by (for example) chromatography or crystallization. Cleavage of the chiral auxiliary, using methods known to cleave the chosen auxiliary (e.g. $LiOH/H_2O_2$ at −50° C. to 50° C. for the Evans auxiliary) then leads to the desired N-protected beta-amino acid with the desired stereochemistry at the beta-position. Additionally, if $R^6$ is also a protecting group (e.g. 2,4-dimethoxybenzyl), it may be removed in the presence of the Boc-group (e.g. hydrogenation or DDQ, etc.) to give the Boc-amino acid, which upon removal of the Boc-group would provide the primary amine, which may be further functionalized by alkylation, acylation or reductive amination (either prior to or after coupling with the pyrimidine-piperazine unit).

Scheme K shows representative methods of forming the single enantiomers of the gamma amino acids wherein $R^c$, $R^d$, and $R^9$ are as defined herein t is 0 to 4, $R^6$ is H, and $R^7$ is an amine protecting group such as Boc. In one possible method, the racemic amino acid is subject to chiral chromatographic separation using a chiral stationary phase. Alternatively, a diastereomeric mixture may be prepared which could be separated by conventional chromatographic techniques. For example, activation of the racemic amino acid (e.g. $COCl_2$, base) and introduction of a chiral auxiliary, R* (e.g. an Evans' oxazolidinone) in the presence of a basic amine (e.g. Hunig's base) at −20° C. to 50° C. gives the diastereomeric mixture. This mixture may be separated using standard conditions (e.g. column chromatography, HPLC, SFC, etc.) to give the individual diastereomers. These may be converted to the desired acids by cleavage of the chiral auxiliary (in the case of an Evans' auxiliary, by using (for example) LiOH/HOOH at −15° C. to room temperature to give the single enantiomers of the gamma-amino acids. The temperature may need to be kept low so as to prevent racemization of the newly separated chiral center.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction

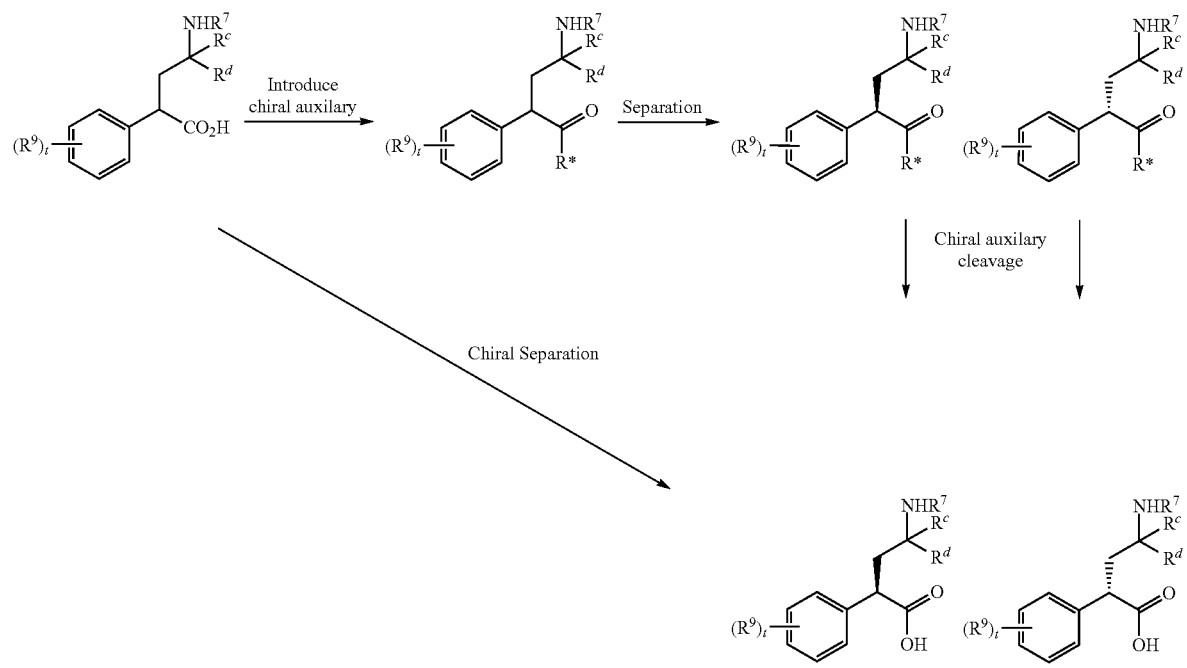

Scheme K products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513: 375-378). Enriched or purified enantiomers can be distinguished by methods used to distinguish other chiral molecules with asymmetric carbon atoms, such as optical rotation and circular dichroism.

Methods of Treatment with Compounds of Formula I

The compounds of the present invention can be used as prophylactics or therapeutic agents for treating diseases or disorders mediated by modulation or regulation of AKT protein kinases, tyrosine kinases, additional serine/threonine kinases, and/or dual specificity kinases. AKT protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of hyperproliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multifonn. oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), multiple sclerosis, obesity, Alzheimer's disease, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Accordingly, another aspect of this invention provides a method of treating diseases or medical conditions in a mammal mediated by AKT protein kinases, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by the activity of one or more AKT protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein. In the case of cancer, an effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

"Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

This invention also provides compounds of Formula I for use in the treatment of AKT protein kinase-mediated conditions.

An additional aspect of the invention is the use of a compound of Formula I in the preparation of a medicament for therapy, such as for the treatment or prevention of AKT protein kinase-mediated conditions.

Combination Therapy

The compounds of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

The second compound of the pharmaceutical combination formulation or dosing regimen preferably has complementary activities to the compound of this invention such that they do not adversely affect each other. Such drugs are suitably present in combination in amounts that are effective for the purpose intended. Accordingly, another aspect of the present invention provides a composition comprising a compound of this invention in combination with a second drug, such as described herein.

A compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

A "chemotherapeutic agent" is a chemical compound useful in the treatment of cancer, regardless of mechanism of action. Chemotherapeutic agents include compounds used in "targeted therapy" and conventional chemotherapy.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Routes of Administration

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of this invention. In certain embodiments, the pharmaceutical composition comprises a compound of Formula I in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention may be prepared for various routes and types of administration. For example, a compound of this invention having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as a compound of Formula I and, optionally, an additional therapeutic agent) to a mammal. The components of the liposome are commonly arranged in a bilayer formation, similar to the lipid arrangement of biological membranes.

Sustained-release preparations of compounds of this invention may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of compounds of this invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of this invention can be used to treat a disorder mediated, for example, by AKT kinase. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a disorder mediated by AKT kinase. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound suitable for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compounds of Formula I are primarily of value as therapeutic agents for use in mammals, they are also useful whenever it is required to control AKT protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

AKT-1 Kinase Assay

The activity of the compounds described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (F1)-GRPRTSSFAEG. A stock solution of 20 µM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in DMSO are prepared. The stock solutions and the control compound are serially diluted 1:2 nine times into DMSO (10 μL of compound+10 μL of DMSO) to give 50× dilution series over the desired dosing range. Next, 2.1-μL aliquots of the compounds in DMSO are transferred to a Costar 3657 plate containing 50 μL of 10.4 μM ATP in 1×IMAP Reaction Buffer containing 1 mM DTT. After thorough mixing, 2.5-μL aliquots are transferred to a Proxy-Plate™-384 F plate.

The assay is initiated by the addition of 2.5-μL aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 μL of Binding Solution, centrifuged again and incubated for an additional 30 minutes at ambient temperature prior to reading on a Victor 1420 Multilabel HTS Counter configured to measure fluorescence polarization.

The compounds of Examples 1-29 were tested in the above assay and found to have an $IC_{50}$ of less than 10 μM.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were recorded on a Varian instrument operating at 400 MHz. $^1$H-NMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

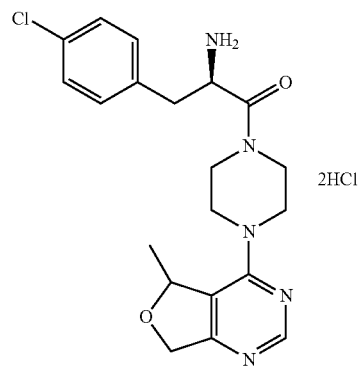

(2R)-2-amino-3-(4-chlorophenyl)-1-(4-(5-methyl-5, 7-dihydrofuro[3,4-d]pyrimidin-4-yl)piperazine-1-yl) propan-1-one dihydrochloride Step 1: A suspension of 60% NaH (11.6 g, 291.4 mmol) in anhydrous ethyl ether (200 mL) was stirred for 10 minutes and then a solution of methyl glycolate (25.0 g, 277.0 mmol) in ethyl ether (50 mL) was added dropwise over 15 minutes. This suspension was diluted with DMSO (200 mL) and cooled to 0° C. A solution of methyl crotanate (33.3 g, 333.0 mmol) in 100 mL of DMSO was added dropwise over 30 minutes and allowed to stir with warming to room temperature overnight. The reaction was quenched by slowing pouring the reaction mixture into water (200 mL) and the acidity was adjusted to pH 2-3 by the addition of 1N HCl. The resulting mixture was extracted with ethyl ether (3×500 mL) and the combined organic layers washed with brine, dried with $MgSO_4$ and concentrated. The crude residue was purified by column chromatography (4:1 Hexane:EtOAc) to give methyl 2-methyl-4-oxotetrahydrofuran-3-carboxylate (32.3 g, 73%) as a clear liquid. $^1$H NMR ($CDCl_3$, 400 MHz) δ 4.54 (dddd, J=8.4, 6.0, 6.0, 6.0 Hz, 1H), 4.19 (d, J=8.8 Hz, 1H), 3.98 (d, J=8.8 Hz, 1H), 3.79 (s, 3H), 3.11 (d, J=8.8 Hz, 1H), 1.49 (d, J=6.0 Hz, 3H).

Step 2: A mixture of methyl 2-methyl-4-oxotetrahydrofuran-3-carboxylate (8.3 g, 52.8 mmol), formamidine (7.0 g, 68.6 mmol) and toluene (200 mL) was heated to reflux under Dean-Stark conditions overnight. The mixture was allowed to cool to room temperature, diluted with water and neutralized by the addition of saturated $Na_2CO_3$. The organic layer was separated and the aqueous layer extracted with EtOAc (5×200 mL). The combined organic layers were dried with brine, $MgSO_4$ and concentrated. The residue was purified by column chromatography (100% EtOAc to 5% MeOH:EtOAc) to give 5-methyl-5,7-dihydrofuro[3,4-d]pyrimidin-4-ol as a brown solid. $^1$H NMR (DMSO-$d_6$, 400 MHz) δ 12.58 (s, 1H), 8.18 (s, 1H), 5.18 (bs, 1H), 4.82 (d, J=14.4 Hz, 1H), 4.72 (d, J=14.4 Hz, 1H), 1.37 (d, J=6.8 Hz, 3H).

Step 3: To a suspension of 5-methyl-5,7-dihydrofuro[3,4-d]pyrimidin-4-ol (1.2 g, 7.9 mmol) in acetonitrile (50 mL) was added via syringe POCl₃ (3.6 g, 23.7 mmol) and the mixture heated to reflux for 3 hours. The mixture was allowed to cool to room temperature and then concentrated. The residue was diluted with EtOAc and quenched by pouring into saturated NaHCO₃. The organic layer was separated and the aqueous layer extracted with EtOAc (3×100 mL). The combined organic layers were dried (MgSO₄) and concentrated to give 4-chloro-5-methyl-5,7-dihydrofuro[3,4-d]pyrimidine (1.3 g, 96%) as a light brown oil which was used in the next step without further purification. ¹H NMR (CDCl₃, 400 MHz) δ 8.89 (s, 1H), 5.46 (q, J=6.4 Hz, 1H), 5.15 (dd, J=14.4, 2.8 Hz, 1H), 5.02 (dd, J=14.4, 2.8 Hz, 1H), 1.62 (d, J=6.4 Hz, 3H).

Step 4: A mixture of 4-chloro-5-methyl-5,7-dihydrofuro[3,4-d]pyrimidine (0.97 g, 5.7 mmol), N-Bocpiperazine (1.3 g, 6.8 mmol), TEA (1.6 mL, 11.4 mmol) and NMP (3 mL) was heated to 90° C. for 4 hours. The reaction was cooled to room temperature and diluted with H₂O and EtOAc. The organic layer was separated and the aqueous layer extracted with EtOAc (3×20 mL). The combined organics were dried with MgSO₄ and concentrated. The residue was purified by column chromatography (EtOAc) to give tert-butyl 4-(5-methyl-5,7-dihydrofuro[3,4-d]pyrimidin-4-yl)piperazine-1-carboxylate (1.5 g, 83%) as an off white solid. ¹H NMR (CDCl₃, 400 MHz) δ 8.54 (s, 1H), 5.57-5.52 (m, 1H), 4.93 (d, J=2.0 Hz, 2H), 3.67-3.45 (m, 8H), 1.48 (s, 9H), 1.41 (d, J=6.0 Hz, 3H). LCMS (APCI+) m/z 321 [M+H⁺].

Step 5: To a solution of tert-butyl 4-(5-methyl-5,7-dihydrofuro[3,4-d]pyrimidin-4-yl)piperazine-1-carboxylate (0.28 g, 0.87 mmol) in DCM (15 mL) was added 4N HCl in dioxane (5 mL). The mixture was stirred at room temperature overnight and then concentrated to give 5-methyl-4-(piperazin-1-yl)-5,7-dihydrofuro[3,4-d]pyrimidine dihydrochloride salt as an off white solid. ¹H NMR (DMSO-d₆, 400 MHz) δ 9.62 (bs, 2H), 8.72 (s, 1H), 5.72-5.71 (m, 1H), 5.55-5.00 (bs, 1H), 4.99-4.89 (m, 2H), 4.05-4.00 (m, 2H), 3.81-3.75 (m, 2H), 3.19-3.18 (m, 4H), 1.32 (d, J=8.4 Hz, 3H). LCMS (APCI+) m/z 221 [M+H⁺].

Step 6: To a solution of D-Boc-4-chlorophenyl aniline (0.033 g, 0.110 mmol), 5-methyl-4-(piperazin-1-yl)-5,7-dihydrofuro[3,4-d]pyrimidine dihydrochloride salt (0.029 mg, 0.100 mmol) and triethylamine (0.033 mL, 0.220 mmol) in DCM (5 mL) was added HATU (0.042 g, 0.110 mmol). The reaction mixture was stirred at room temperature overnight. The reaction was partitioned between water and DCM and the organic layer separated. The aqueous phase was extracted with DCM (2×10 mL). The combined organic layers were washed with brine, dried with MgSO₄ and concentrated. The residue was purified by column chromatography (EtOAc) to give the coupled intermediate as a clear oil. The material was redissolved in DCM (5 mL) to which was added 4N HCl in dioxane (1 mL). The mixture was stirred at room temperature overnight and then concentrated to give (2R)-2-amino-3-(4-chlorophenyl)-1-(4-(5-methyl-5,7-dihydrofuro[3,4-d]pyrimidin-4-yl)piperazine-1-yl)propan-1-one dihydrochloride salt as an off white solid (0.030 mg, 60%). ¹H NMR (CD₃OD, 400 MHz) δ 8.70 (s, 1H), 7.41 (dd, J=8.4, 3.6 Hz, 2H), 7.31 (dd, J=8.4, 3.6 Hz, 2H), 5.75 (bs, 1H), 5.12-50.2 (m, 2H), 4.70 (dd, J=7.2, 7.2 Hz, 1H), 4.01-3.15 (m, 11H), 1.42 (d, J=6.4, 6.4 Hz, 3H). LCMS (APCI+) m/z 402 [M+H⁺].

Example 2

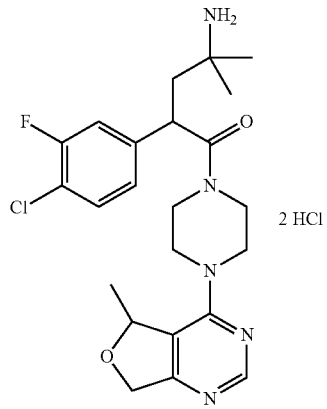

4-amino-2-(4-chloro-3-fluorophenyl)-4-methyl-1-(4-(5-methyl-5,7-dihydrofuro[3,4-d]pyrimidin-4-yl)piperazin-1-yl)pentan-1-one dihydrochloride Step 1: Methyl 2-(4-chloro-3-fluorophenyl)acrylate (1.00 g, 4.66 mmol) and 2-nitropropane (502 uL, 5.59 mmol) were dissolved in MeCN (16 mL) and treated with DBU (835 uL, 5.59 mmol) at room temperature. The mixture was allowed to stir over the weekend to completion. The mixture was poured into 1M HCl solution and extracted with ethyl acetate (2×). The combined organic portions were washed with water (1×), then brine, separated, dried over MgSO₄, filtered, and concentrated in vacuo to yield methyl 2-(4-chloro-3-fluorophenyl)-4-methyl-4-nitropentanoate (1.51 g).

Step 2: Methyl 2-(4-chloro-3-fluorophenyl)-4-methyl-4-nitropentanoate (1.51 g, 4.97 umol) and Zn dust (6.50 g, 99.4 mmol) were dissolved/suspended in ethanol (25 mL) and treated with concentrated HCl (1.37 mL, 16.4 mmol) at 40° C. The mixture was heated to reflux for several hours to completion and was allowed to cool to room temperature. The mixture was then filtered through a plug of celite with more ethanol. The filtrate was concentrated in vacuo, then poured into half saturated NaHCO₃ solution. The aqueous portion was extracted several times with ethyl acetate, and the organics were combined. The organic portion was washed with water (1×), then brine, separated, dried over MgSO₄, filtered, and concentrated in vacuo to afford the near-pure product as a solid. The material was partially suspended/dissolved in a minimal amount of ethyl acetate and diluted with hexanes. The resulting 3-(4-chloro-3-fluorophenyl)-5,5-dimethylpyrrolidin-2-one was isolated by vacuum filtration (826 mg, 69%).

Step 3: The 3-(4-chloro-3-fluorophenyl)-5,5-dimethylpyrrolidin-2-one (826 mg, 3.42 mmol) was dissolved in THF (20 mL) and cooled to −78° C. under nitrogen. LiHMDS (3.76 mL, 3.76 mmol) was added via syringe, and the solution was allowed to stir for 30 minutes. The mixture was quenched with the addition of Boc2O (942 uL, 4.10 mmol) via syringe. The mixture was allowed to warm slowly to room temperature over a 2 hour period. The reaction was poured into 0.5M HCl solution and extracted with ethyl acetate (2×). The combined organic was washed with water (2×), then brine, separated, dried over MgSO₄, filtered, and concentrated in vacuo to afford tert-butyl 4-(4-chloro-3-fluorophenyl)-2,2-dimethyl-5-oxopyrrolidine-1-carboxylate as a colorless oil.

Step 4: tert-Butyl 4-(4-chloro-3-fluorophenyl)-2,2-dimethyl-5-oxopyrrolidine-1-carboxylate (1.168 g, 3.42 mmol, theor.) was dissolved in 4 mL of each: THF, MeOH, water. The LiOH—H₂O (574 mg, 13.7 mmol) was added in one sum to the stirring solution. The reaction mixture was allowed to stir to completion overnight. The reaction mixture was concentrated, and the residue was partitioned between ether and water. The aqueous portion was washed again with ether (both discarded) and then treated with 3N HCl solution until a pH of about 2 to about 3 was achieved. The aqueous portion was extracted with ether several times, and the organics were combined. The organic portion was washed with brine, separated, dried over MgSO$_4$, filtered, and concentrated in vacuo to afford 4-(tert-butoxycarbonylamino)-2-(4-chloro-3-fluorophenyl)-4-methylpentanoic acid as a white solid (1.06 g, 86%).

Step 5: To a solution of 4-(tert-butoxycarbonylamino)-2-(4-chloro-3-fluorophenyl)-4-methylpentanoic acid (0.038 g, 0.110 mmol), 5-methyl-4-(piperazin-1-yl)-5,7-dihydrofuro[3,4-d]pyrimidine dihydrochloride salt (0.029 mg, 0.100 mmol) and triethylamine (0.033 mL, 0.220 mmol) in DCM (5 mL) was added HATU (0.042 g, 0.110 mmol). The reaction mixture was stirred at room temperature overnight. The mixture was partitioned between water and DCM and the organic layer separated. The aqueous phase was extracted with DCM (2×10 mL). The combined organic layers were washed with brine, dried with MgSO$_4$ and concentrated. The residue was purified by column chromatography (EtOAc) to give the coupled intermediate as a clear oil. The material was redissolved in DCM (5 mL) to which was added 4N HCl in dioxane (1 mL). The mixture was stirred at room temperature overnight and then concentrated to give 4-amino-2-(4-chloro-3-fluorophenyl)-4-methyl-1-(4-(5-methyl-5,7-dihydrofuro[3,4-d]pyrimidin-4-yl)piperazin-1-yl)pentan-1-one dihydrochloride salt as an off white solid (0.033 mg, 61%). $^1$H NMR (CD$_3$OD, 400 MHz) δ 8.67 (s, 1H), 7.52-7.51 (m, 1H), 7.30-7.28 (m, 1H), 7.13-7.08 (m, 1H), 5.76-5.73 (m, 1H), 5.11-5.01 (m, 2H), 4.40-4.38 (m, 1H), 3.93-3.49 (m, 10H), 1.43-1.33 (m, 9H). LCMS (APCI+) m/z 462 [M+H$^+$].

Example 3

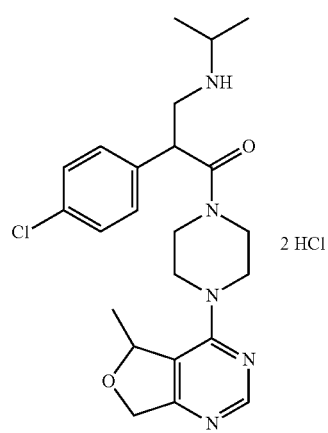

2-(4-chlorophenyl)-3-(isopropylamino)-1-(4-(5-methyl-5,7-dihydrofuro[3,4-d]pyrimidin-4-yl)piperazine-1-yl)propan-1 one dihydrochloride Step 1: Methyl 2-(4-chlorophenyl)acrylate (1.00 g, 5.09 mmol) was added as a solution in THF (2.5 mL) to a stirring solution of i-PrNH$_2$ (650 uL, 7.63 mmol) in THF (10 mL) The reaction was allowed to stir at room temperature overnight to completion by LCMS analysis. The solvent was removed under reduced pressure to give methyl 2-(4-chlorophenyl)-3-(isopropylamino)propanoate (LCMS (APCI$^+$) [M-Boc+H]$^+$ 256.1, Rt: 1.97 min), which was re-dissolved in DCM (15 mL) at room temperature. The Boc2O (1.29 mL, 5.59 mmol) was added to the stirring amine via pipette followed by a catalytic amount (1 mg) of DMAP. The reaction was allowed to stir overnight to completion by LCMS and TLC analysis of the mixture. The solution was concentrated in vacuo to afford methyl 3-(tert-butoxycarbonyl(isopropy)amino)-2-(4-chlorophenyl)propanoate as an oily residue (LCMS (APCI$^+$) [M-Boc+H]$^+$ 256.1, Rt: 4.13 min) which was re-dissolved in THF (12.0 mL) and water (4.0 mL). The solution was treated with LiOH—H$_2$0 (1.07 g, 25.4 mmol) and allowed to stir for 4 hours to completion by LCMS analysis. The solution was diluted with water and washed with diethyl ether (discarded). The aqueous was treated with 1M HCl solution until a pH of about 2 to about 3 was achieved and extracted with ethyl acetate several times. The organics were combined, washed with brine, separated, dried over MgSO$_4$, filtered, and concentrated in vacuo to afford 3-(tert-butoxycarbonyl(isopropyl)amino)-2-(4-chlorophenyl)propanoic acid as an oil (1.04 g, 60%). LCMS (APCI$^+$) [M-Boc+H]$^+$ 242.0.

Step 2: To a solution of 3-(tert-butoxycarbonyl(isopropyl)amino)-2-(4-chlorophenyl)propanoic acid (0.037 g, 0.110 mmol), 5-methyl-4-(piperazin-1-yl)-5,7-dihydrofuro[3,4-d]pyrimidine dihydrochloride salt (0.029 mg, 0.100 mmol), and triethylamine (0.033 mL, 0.220 mmol) in DCM (5 mL) was added HATU (0.042 g, 0.110 mmol). The reaction mixture was stirred at room temperature overnight. The mixture was partitioned between water and DCM and the organic layer separated. The aqueous phase was extracted with DCM (2×10 mL). The combined organic layers were washed with brine, dried with MgSO$_4$ and concentrated. The residue was purified by column chromatography (EtOAc) to give the coupled intermediate as clear oil. The oil was redissolved in DCM (5 mL) to which was added 4N HCl in dioxane (1 mL) and the reaction mixture was stirred at room temperature overnight. The reaction mixture was concentrated to give 2-(4-chlorophenyl)-3-(isopropylamino)-1-(4-(5-methyl-5,7-dihydrofuro[3,4-d]pyrimidin-4-yl)piperazine-1-yl)propan-1 one dihydrochloride salt as an off white solid (0.030 mg, 60%). $^1$H NMR (CD$_3$OD, 400 MHz) δ 8.66 (s, 1H), 7.47-7.46 (m, 2H), 7.44-7.37 (m, 2H), 5.72 (bs, 1H), 5.10-5.00 (m, 2H), 4.51-4.47 (m, 1H), 3.85-2.81 (m, 11H), 1.42-1.35 (m, 9H). LCMS (APCI+) m/z 444.2 [M+H$^+$].

Example 4

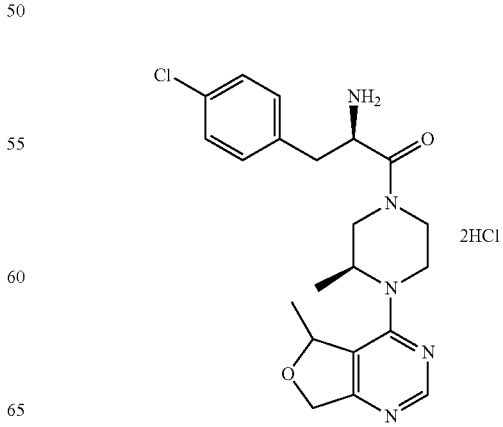

(2R)-2-amino-3-(4-chlorophenyl)-1-((3S)-3-methyl-4-(5-methyl-5,7-dihydrofuro[3,4-d]pyrimidin-4-yl)piperazin-1-yl)propane-1-one dihydrochloride Step 1: A mixture of 4-chloro-5-methyl-5,7-dihydrofuro[3,4-d]pyrimidine (0.340 g, 1.99 mmol), (S)-tert-butyl-3-methylpiperazine-1-carboxylate (0.439, 2.19 mmol), TEA (0.56 mL, 4.0 mmol) and NMP (3 mL) was heat to 90° C. for 4 hours. The reaction was cooled to room temperature and diluted with H$_2$O and EtOAc. The organic layer was separated and the aqueous layer extracted with EtOAc (3×20 mL). The combined organics were dried with MgSO$_4$ and concentrated. The residue was purified by column chromatography (EtOAc) to give (3S)-tert-butyl 3-methyl-4-(5-methyl-5,7-dihydrofuro[3,4-d]pyrimidin-4-yl)piperazine-1-carboxylate (0.590 g, 89%) as an off white solid. LCMS (APCI+) m/z 235 [M-C$_5$H$_9$O$_2$+H$^+$]; Rt=2.71 min. This material was dissolved in DCM (5 mL) to which was added excess 4 N HCl in dioxane (2 mL) and the reaction allowed to stir at room temperature overnight. The reaction was concentrated to give 5-methyl-4-((S)-2-methylpiperazin-1-yl)-5,7-dihydrofuro[3,4-d]pyrimidine dihydrochloride (0.540 g, 93%) was an off white solid. $^1$H NMR (CD$_3$OD, 400 MHz) δ 8.82 (s, 1H), 5.83-5.79 (m, 1H), 5.18-5.05 (m, 1H), 4.48-4.36 (m, 1H), 3.87-3.73 (m, 1H), 3.58-3.52 (m, 1H), 3.48-3.43 (m, 3H), 1.51-1.46 (m, 5H). LCMS (APCI+) m/z 235 [M+H$^+$]; Rt=1.13 min.

Step 2: To a solution of D-Boc-4-chlorophenyl alanine (0.033 g, 0.110 mmol), 5-methyl-4-((S)-2-methylpiperazin-1-yl)-5,7-dihydrofuro[3,4-d]pyrimidine dihydrochloride (0.031 mg, 0.100 mmol), and triethylamine (0.033 mL, 0.220 mmol) in DCM (3 mL) was added HATU (0.042 g, 0.110 mmol). The reaction mixture was stirred at room temperature overnight. The mixture was partitioned between water and DCM and the organic layer separated. The aqueous phase was extracted with DCM (2×10 mL). The combined organic layers were washed with brine, dried with MgSO$_4$ and concentrated. The residue was purified by column chromatography (EtOAc) to give the coupled intermediate tert-butyl(2R)-3-(4-chlorophenyl)-1-((3S)-3-methyl-4-(5-methyl-5,7-dihydrofuro[3,4-d]pyrimidin-4-yl)piperazin-1-yl)-1-oxopropan-2-ylcarbamate LCMS (APCI+) m/z 516 [M+H$^+$]; Rt=3.18 min as a clear oil. This material was dissolved in DCM (5 mL) to which was added excess 4N HCl in dioxane (2 mL). The mixture was stirred at room temperature overnight and then evaporated. The residue was dissolved in a minimal amount of isopropanol and titrated with ether to form a white precipitate, which was filtered to give (2R)-2-amino-3-(4-chlorophenyl)-1-((3S)-3-methyl-4-(5-methyl-5,7-dihydrofuro[3,4-d]pyrimidin-4-yl)piperazin-1-yl)propane-1-one dihydrochloride as an off white solid (0.025 mg, 51%). $^1$H NMR (CD$_3$OD, 400 MHz) δ 8.71 (s, 1H), 7.41-7.26 (m, 4H), 5.73-5.71 (m, 1H), 5.12-5.01 (m, 2H), 4.39-4.32 (m, 1H), 4.10-4.05 (m, 1H), 3.95-3.81 (m, 1H), 3.67-3.48 (m, 2H), 3.23-3.01 (m, 3H), 2.73-2.58 (m, 1H), 1.45-1.26 (m, 6H), 1.15-1.41 (d, J=6.0 Hz, 3H). LCMS (APCI+) m/z 416 [M+H$^+$]; Rt=2.18 min.

The following compounds were also prepared using the above-described methods.

Example 5

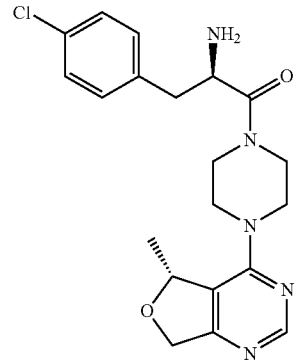

(R)-2-amino-3-(4-chlorophenyl)-1-(4-((R)-5-methyl-5,7-dihydrofuro[3,4-d]pyrimidin-4-yl)piperazin-1yl)propan-1-one

LCMS: 402.1 [M+H$^+$] (APCI+).

Example 6

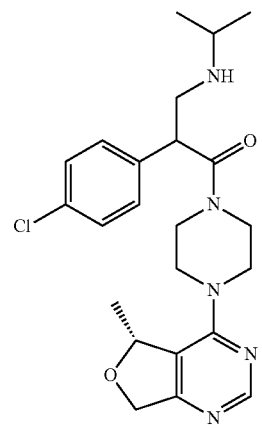

2-(4-chlorophenyl)-3-(isopropylamino)-1-(4-((R)-5-methyl-5,7-dihydrofuro[3,4-d]pyrimidin-4-yl)piperazin-1-yl)propan-1-one $^1$H NMR (CD$_3$OD): 8.65 (1H, app d, J 1.9 Hz), 7.47-7.37 (4H, m), 5.73 (1H, app br s), 5.05 (2H, app q, J 13.1 Hz), 4.60-4.55 (1H, m), 4.21-3.16 (12H, m), 1.43-1.34 (9H, m). LCMS: 444.1 [M+H$^+$] (APCI+).

Example 7

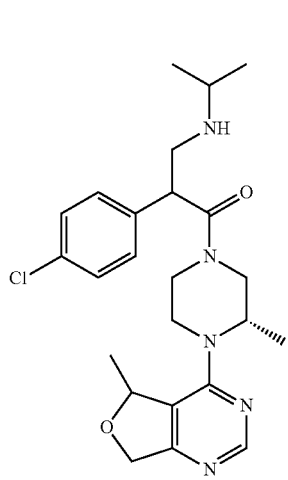

2-(4-chlorophenyl)-3-(isopropylamino)-1-((3S)-3-methyl-4-(5-methyl-5,7-dihydrofuro[3,4-d]pyrimidin-4-yl)piperazin-1-yl)propan-1-one

LCMS: 458.1 [M+H$^+$] (APCI+).

Example 8

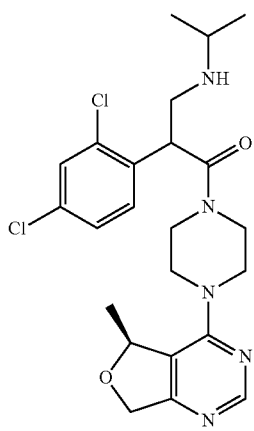

2-(2,4-dichlorophenyl)-3-(isopropylamino)-1-(4-((S)-5-methyl-5,7-dihydrofuro[3,4-d]pyrimidin-4-yl)piperazin-1-yl)propan-1-one

LCMS: 478.1 [M+H$^+$] (APCI+).

Example 9

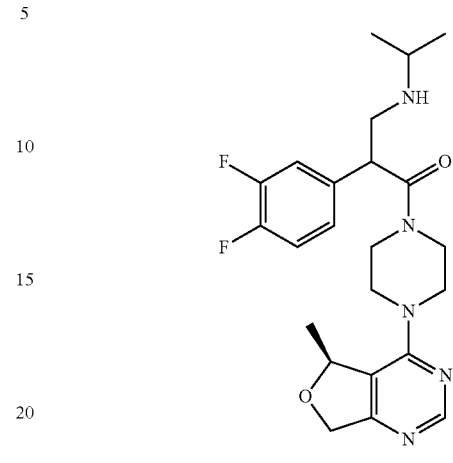

2-(3,4-difluorophenyl)-3-(isopropylamino)-1-(4-((S)-5-methyl-5,7-dihydrofuro[3,4-d]pyrimidin-4-yl)piperazin-1-yl)propan-1-one $^1$H NMR (CD$_3$OD): 8.64 (1H, app d, J 2.3 Hz), 7.37-7.27 (2H, m), 7.24-7.17 (1H, m), 5.72 (1H, app br s), 5.03 (2H, app q, J 13.6 Hz), 4.63-4.56 (1H, m), 4.19-4.02 (1H, m), 3.93-3.10 (11H, m), 1.41-1.33 (9H, m). LCMS: 446.2 [M+H$^+$] (APCI+).

Example 10

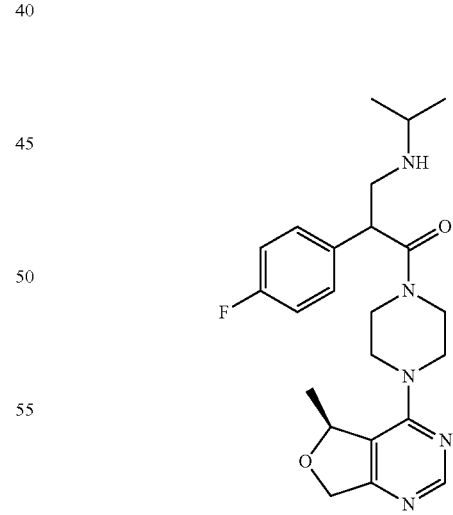

2-(4-fluorophenyl)-3-(isopropylamino)-1-(4-((S)-5-methyl-5,7-dihydrofuro[3,4-d]pyrimidin-4-yl)piperazin-1-yl)propan-1-one

LCMS: 428.2 [M+H$^+$] (APCI+).

Example 11

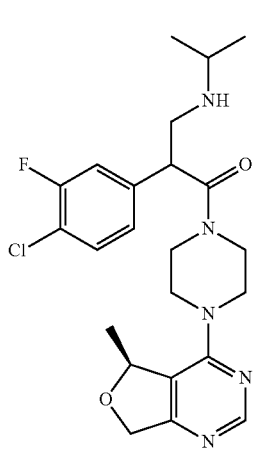

2-(4-chloro-3-fluorophenyl)-3-(isopropylamino)-1-(4-((S)-5-methyl-5,7-dihydrofuro[3,4-d]pyrimidin-4-yl)piperazin-1-yl)propan-1-one ¹H NMR (CD₃OD): 8.45 (1H, app d, J 12 Hz), 7.53-7.44 (1H, m), 7.17-7.05 (2H, m), 5.64-5.58 (1H, m), 5.04-4.95 (2H, m), 4.35 (1H, br s), 4.08-3.00 (12H, m), 1.33-1.11 (9H, m). LCMS: 462.1 [M+H⁺] (APCI+).

Example 12

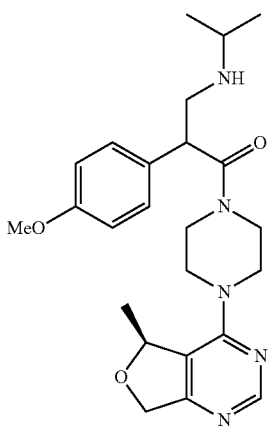

3-(isopropylamino)-2-(4-methoxyphenyl)-1-(4-((S)-5-methyl-5,7-dihydrofuro[3,4-d]pyrimidin-4-yl)piperazin-1-yl)propan-1-one

LCMS: 440.2 [M+H⁺] (APCI+).

Example 13

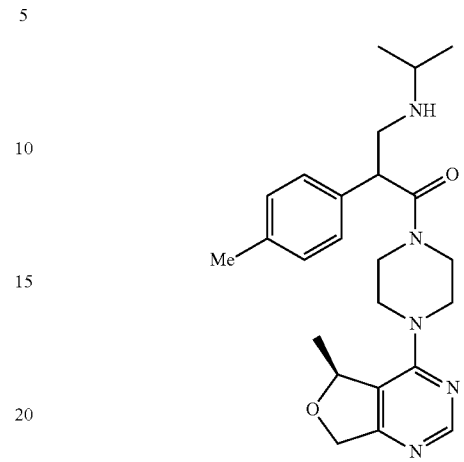

3-(isopropylamino)-1-(4-((S)-5-methyl-5,7-dihydrofuro[3,4-d]pyrimidin-4-yl)piperazin-1-yl)-2-p-tolyl-propan-1-one ¹H NMR (CD₃OD): 8.44 (1H, app d, J 9.8 Hz), 7.21-7.11 (4H, m), 5.51-5.63 (1H, m), 5.03-4.94 (2H, m), 4.30-4.25 (1H, m), 4.20-2.80 (12H, m), 2.21 (3H, s), 1.26-1.17 (9H, m). LCMS: 424.2 [M+H⁺] (APCI+).

Example 14

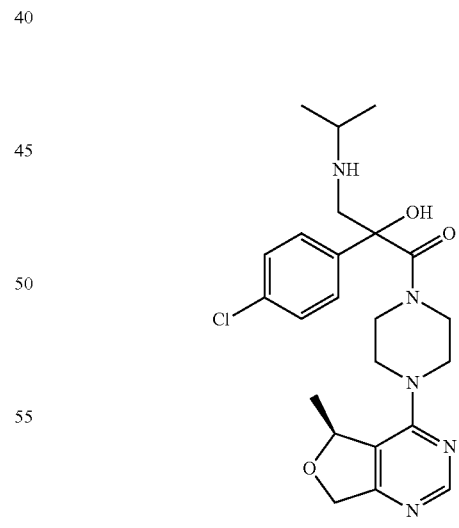

2-(4-chlorophenyl)-2-hydroxy-3-(isopropylamino)-1-(4-((S)-5-methyl-5,7-dihydrofuro[3,4-d]pyrimidin-4-yl)piperazin-1-yl)propan-1-one

LCMS: 460.2 [M+H⁺] (APCI+).

Example 15

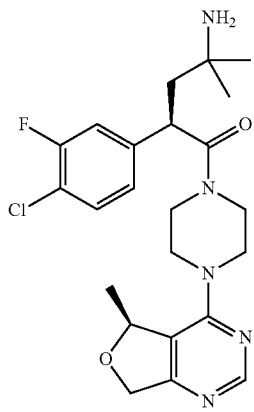

(R)-4-amino-2-(4-chloro-3-fluorophenyl)-4-methyl-1-(4-((S)-5-methyl-5,7-dihydrofuro[3,4-d]pyrimidin-4-yl)piperazin-1-yl)pentan-1-one

LCMS: 462 [M+H$^+$] (APCI+).

Example 16

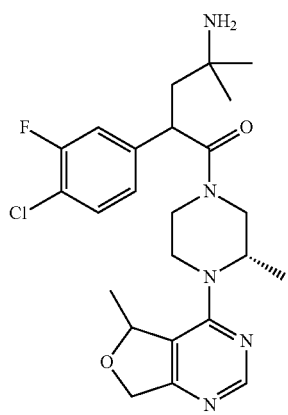

4-amino-2-(4-chloro-3-fluorophenyl)-4-methyl-1-((3S)-3-methyl-4-(5-methyl-5,7-dihydrofuro[3,4-d]pyrimidin-4-yl)piperazin-1-yl)pentan-1-one

LCMS: 476.1 [M+H$^+$] (APCI+).

Example 17

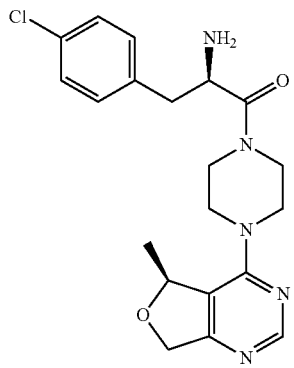

(R)-2-amino-3-(4-chlorophenyl)-1-(4-((S)-5-methyl-5,7-dihydrofuro[3,4-d]pyrimidin-4-yl)piperazin-1-yl)propan-1-one $^1$H NMR (CD$_3$OD): 8.68 (1H, app d, J 3.9 Hz), 7.38 (2H, d, J 8.3 Hz), 7.31 (2H, d, J 7.0 Hz), 5.78-5.70 (1H, m), 5.07 (2H, app q, J 13.3 Hz), 4.80-4.71 (1H, m), 4.10-3.06 (12H, m), 1.39 (3H, d, J 6.1 Hz). LCMS: 402.1 [M+H$^+$] (APCI+).

Example 18

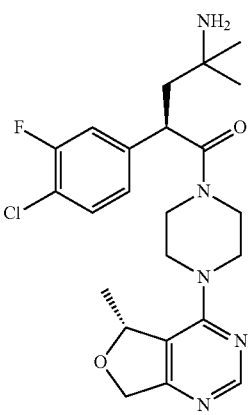

(R)-4-amino-2-(4-chloro-3-fluorophenyl)-4-methyl-1-(4-((R)-5-methyl-5,7-dihydrofuro[3,4-d]pyrimidin-4-yl)piperazin-1-yl)pentan-1-one

LCMS: 462.1 [M+H$^+$] (APCI+).

Example 19

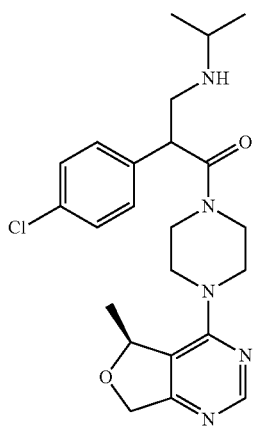

2-(4-chlorophenyl)-3-(isopropylamino)-1-(4-((S)-5-methyl-5,7-dihydrofuro[3,4-d]pyrimidin-4-yl)piperazin-1-yl)propan-1-one

LCMS: 444.1 [M+H$^+$] (APCI+).

Example 20

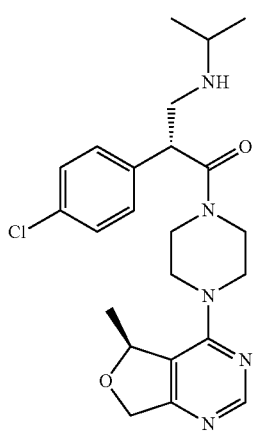

(R)-2-(4-chlorophenyl)-3-(isopropylamino)-1-(4-((S)-5-methyl-5,7-dihydrofuro[3,4-d]pyrimidin-4-yl)piperazin-1-yl)propan-1-one

LCMS: 444.1 [M+H$^+$] (APCI+).

Example 21

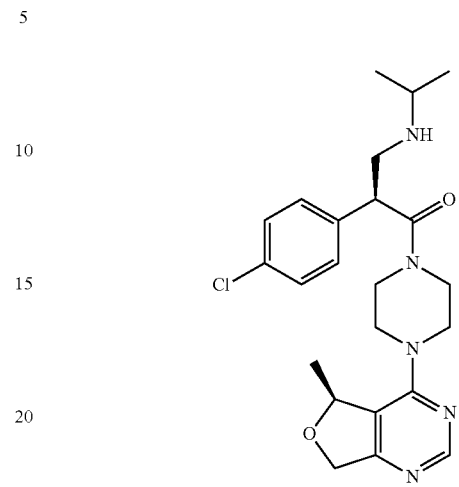

(S)-2-(4-chlorophenyl)-3-(isopropylamino)-1-(4-((S)-5-methyl-5,7-dihydrofuro[3,4-d]pyrimidin-4-yl)piperazin-1-yl)propan-1-one

LCMS: 444.2 [M+H$^+$] (APCI+).

Example 22

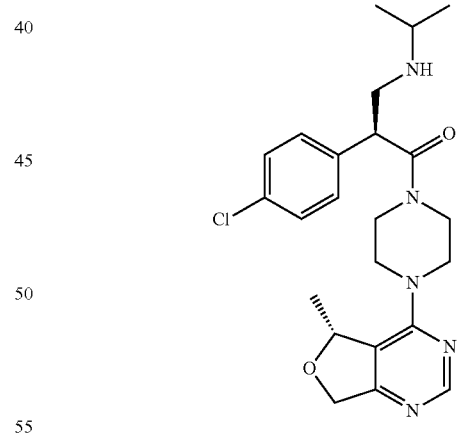

(S)-2-(4-chlorophenyl)-3-(isopropylamino)-1-(4-((R)-5-methyl-5,7-dihydrofuro[3,4-d]pyrimidin-4-yl)piperazin-1-yl)propan-1-one $^1$H NMR (CD$_3$OD): 8.66 (1H, s, 7.45 (2H, d, J 8.3 Hz), 7.39 (2H, d, J 8.7 Hz), 5.76-5.68 (1H, m), 5.05 (2H, app q, J 13.5 Hz), 4.60-4.54 (1H, m), 4.11-3.13 (12H, m), 1.42 (3H, d, J 6.0 Hz), 1.37 (6H, d, J 6.6 Hz). LCMS: 444.2 [M+H$^+$] (APCI+).

Example 23

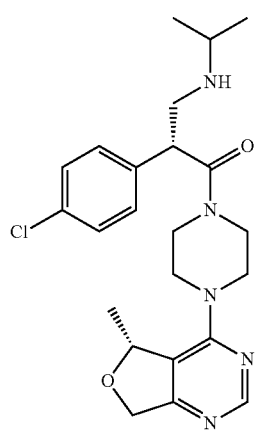

(R)-2-(4-chlorophenyl)-3-(isopropylamino)-1-(4-((R)-5-methyl-5,7-dihydrofuro[3,4-d]pyrimidin-4-yl)piperazin-1-yl)propan-1-one

LCMS: 444.2 [M+H$^+$] (APCI+).

Example 24

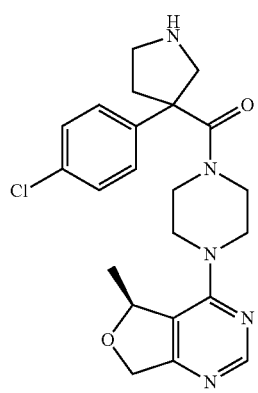

(3-(4-chlorophenyl)pyrrolidin-3-yl)(4-((S)-5-methyl-5,7-dihydrofuro[3,4-d]pyrimidin-4-yl)piperazin-1-yl)methanone

LCMS: 428.2 [M+H$^+$] (APCI+).

Example 25

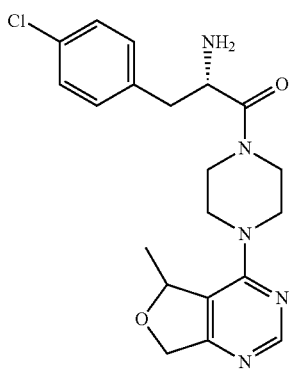

(2S)-2-amino-3-(4-chlorophenyl)-1-(4-(5-methyl-5,7-dihydrofuro[3,4-d]pyrimidin-4-yl)piperazin-1-yl)propan-1-one $^1$H NMR (CD$_3$OD): 8.70 (s, 1H), 7.41 (dd, J=8.4, 3.6 Hz, 2H), 7.31 (dd, J=8.4, 3.6 Hz, 2H), 5.75 (bs, 1H), 5.12-50.2 (m, 2H), 4.70 (dd, J=7.2, 7.2 Hz, 1H), 4.01-3.15 (m, 12H), 1.42 (dd, J=6.4, 6.4 Hz, 3H). LCMS: 402.2 [M+H$^+$] (APCI+).

Example 26

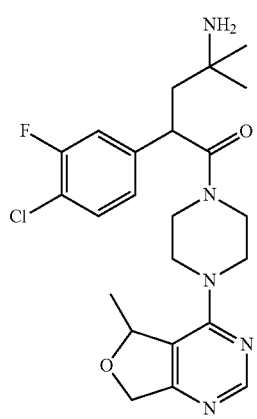

4-amino-2-(4-chloro-3-fluorophenyl)-4-methyl-1-(4-(5-methyl-5,7-dihydrofuro[3,4-d]pyrimidin-4-yl)piperazin-1-yl)pentan-1-one $^1$H NMR (CD$_3$OD): 8.67 (s, 1H), 7.52-7.51 (m, 1H), 7.30-7.28 (m, 1H), 7.13-7.08 (m, 1H), 5.76-5.73 (m, 1H), 5.11-5.01 (m, 2H), 4.40-4.38 (m, 1H), 3.93-3.49 (m, 12H), 1.43-1.33 (m, 9H). LCMS: 462.1 [M+H$^+$] (APCI+).

Example 27

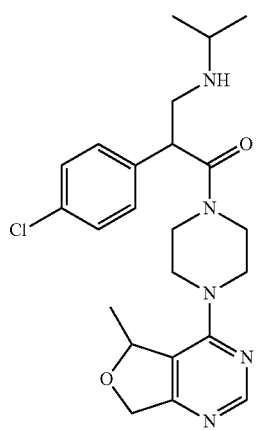

2-(4-chlorophenyl)-3-(isopropylamino)-1-(4-(5-methyl-5,7-dihydrofuro[3,4-d]pyrimidin-4-yl)piperazin-1-yl)propan-1-one $^1$H NMR (CD$_3$OD): 8.66 (s, 1H), 7.47-7.46 (m, 2H), 7.44-7.37 (m, 2H), 5.72 (bs, 1H), 5.10-5.00 (m, 2H), 4.51-4.47 (m, 1H), 3.85-2.81 (m, 12H), 1.42-1.35 (m, 9H). LCMS: 444.2 [M+H$^+$] (APCI+).

Example 28

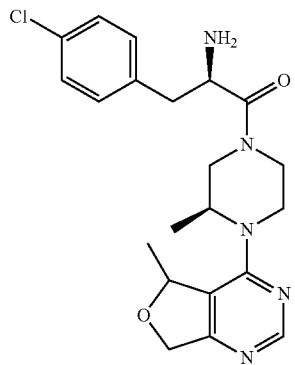

(2R)-2-amino-3-(4-chlorophenyl)-1-((3S)-3-methyl-4-(5-methyl-5,7-dihydrofuro[3,4-d]pyrimidin-4-yl)piperazin-1-yl)propan-1-one $^1$H NMR (CD$_3$OD): 8.71 (s, 1H), 7.41-7.26 (m, 4H), 5.73-5.71 (m, 1H), 5.12-5.01 (m, 2H), 4.39-4.32 (m, 1H), 4.10-4.05 (m, 1H), 3.95-3.81 (m, 1H), 3.67-3.48 (m, 2H), 3.23-3.01 (m, 3H), 2.73-2.58 (m, 1H), 1.45-1.26 (m, 6H), 1.15-1.41 (d, J=6.0H). LCMS: 416.1 [M+H$^+$] (APCI+).

Example 29

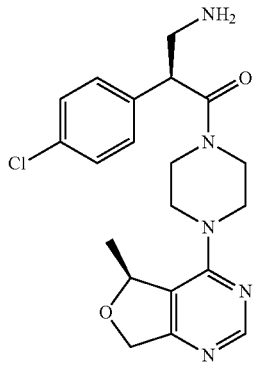

(S)-3-amino-2-(4-chlorophenyl)-1-(4-((S)-5-methyl-5,7-dihydrofuro[3,4-d]pyrimidin-4-yl)piperazin-1-yl)propan-1-one LC/MS (APCI+) m/z 444.2 [M+H]+.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A compound of Formula I:

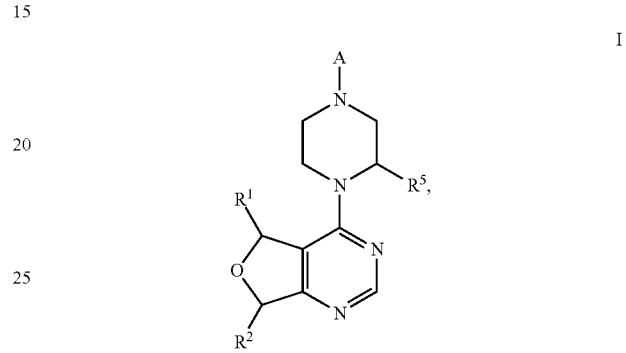

a tautomer, a resolved enantiomer, a diastereomer, or a salt thereof
wherein:
R$^1$ is H, methyl (Me), ethyl (Et), propyl, isopropyl, cyclopropyl, CF$_3$, CHF$_2$ or CH$_2$F;
R$^2$ is H or Me;
R$^5$ is H, Me, Et, or CF$_3$;
A is

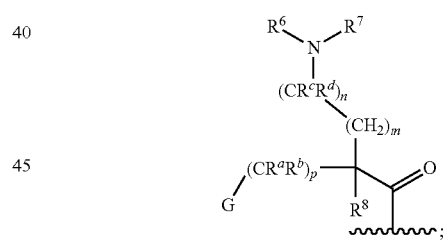

G is phenyl optionally substituted independently with one to four R$^9$ groups;
R$^6$ and R$^7$ are independently H, (C$_3$-C$_6$ cycloalkyl)-(CH$_2$), (C$_3$-C$_6$ cycloalkyl)-(CH$_2$CH$_2$), V—(CH$_2$)$_{0-1}$ wherein V is a 5-6 membered heteroaryl, W—(CH$_2$)$_{1-2}$ wherein W is phenyl optionally substituted with F, Cl, Br, I, OMe, CF$_3$ or Me, C$_3$-C$_6$-cycloalkyl, hydroxy-(C$_3$-C$_6$-cycloalkyl), fluoro-(C$_3$-C$_6$-cycloalkyl), CH(CH$_3$)CH(OH)phenyl, 4-6 membered heterocycle optionally substituted with F, OH, cyclopropylmethyl, —C$_1$-C$_3$ alkyl, C(=O)(C$_1$-C$_3$ alkyl, or C(=O)(C$_1$-C$_3$ alkyl) or C$_1$-C$_6$-alkyl optionally substituted with one or more groups independently selected from the group consisting of OH, O(C$_1$-C$_6$-alkyl), CN, F, NH$_2$, NH(C$_1$-C$_6$-alkyl), N(C$_1$-C$_6$-alkyl)$_2$, tetrahydropyranyl, tetrahydrofuranyl, morpholinyl, oxetanyl, piperidinyl, and pyrrolidinyl,
or R$^6$ and R$^7$ together with the nitrogen to which they are attached form a 4-6 membered heterocyclic ring optionally substituted with one or more groups independently selected from the group consisting of OH, halogen, oxo, $CF_3$, $CH_2CF_3$, and $(C_1-C_3)$alkyl;

$R^a$ and $R_b$ are H, or $R^a$ is H, and $R_b$ and $R^6$ together with the atoms to which they are attached form a 5-6 membered heterocyclic ring having one or two ring nitrogen atoms;

$R^c$ and $R_d$ are H or Me, or $R_c$ and $R_d$ together with the atom to which they are attached form a cyclopropyl ring;

$R^8$ is H, Me, or OH, or $R^8$ and $R^6$ together with the atoms to which they are attached form a 5-6 membered heterocyclic ring having a ring nitrogen atom;

each $R^9$ is independently halogen, $C_1-C_6$-alkyl, $C_3-C_6$-cycloalkyl, O—($C_1-C_6$-alkyl), $CF_3$, $OCF_3$, S($C_1-C_6$-alkyl), CN, $OCH_2$-phenyl, $NH_2$, NH—($C_1-C_6$-alkyl), N—($C_1-C_6$-alkyl)$_2$, piperidine, pyrrolidine, $CH_2F$, $CHF_2$, $OCH_2F$, $OCHF_2$, OH, $SO_2(C_1-C_6$-alkyl), C(O)$NH_2$, C(O)NH($C_1-C_6$-alkyl), and C(O)N($C_1-C_6$-alkyl)$_2$; or m, n and p are independently 0 or 1.

2. A compound of Formula I:

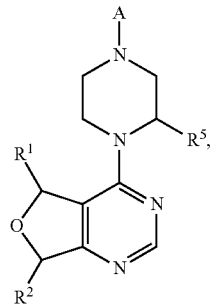

I a tautomer, a resolved enantiomer, a diastereomer, or a salt thereof, wherein:

$R^1$ is H, methyl, ethyl, propyl, isopropyl, cyclopropyl, $CF_3$, $CHF_2$ or $CH_2F$;

$R^2$ is H or Me;

$R^5$ is H, Me, Et, or $CF_3$;

A is

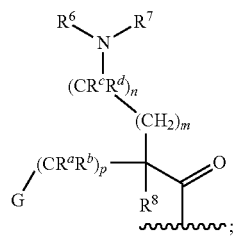

G is phenyl optionally substituted independently with one to four $R^9$ groups;

$R^6$ and $R^7$ are independently H, ($C_3-C_6$ cycloalkyl)-($CH_2$), ($C_3-C_6$ cycloalkyl)-($CH_2CH_2$), V—($CH_2$)$_{0-1}$ wherein V is a 5-6 membered heteroaryl, W—($CH_2$)$_{1-2}$ wherein W is phenyl optionally substituted with F, Cl or Me, $C_3-C_6$-cycloalkyl, hydroxy-($C_3-C_6$-cycloalkyl), fluoro-($C_3$-$C_6$-cycloalkyl), $CH(CH_3)CH(OH)$phenyl, or $C_1-C_6$-alkyl optionally substituted with one or more groups independently selected from the group consisting of OH, O($C_1-C_6$-alkyl), CN, F, $NH_2$, NH($C_1-C_6$-alkyl), N($C_1-C_6$-alkyl)$_2$, piperidinyl, and pyrrolidinyl, or $R^6$ and $R^7$ together with the nitrogen to which they are attached form a 4-6 membered heterocyclic ring optionally substituted with one or more groups independently selected from OH, halogen, oxo, $CF_3$, $CH_2CF_3$, and $(C_1-C_3)$alkyl;

$R_a$ and $R_b$ are H, or $R_a$ is H, and $R_b$ and $R^6$ together with the atoms to which they are attached form a 5-6 membered heterocyclic ring having one or two ring nitrogen atoms;

$R_c$ and $R_d$ are H or Me, or $R_c$ and $R_d$ together with the atom to which they are attached form a cyclopropyl ring;

$R^8$ is H, Me, or OH, or $R^8$ and $R^6$ together with the atoms to which they are attached form a 5-6 membered heterocyclic ring having a ring nitrogen atom;

each $R^9$ is independently halogen, $C_1-C_6$-alkyl, $C_3-C_6$-cycloalkyl, O—($C_1-C_6$-alkyl), $CF_3$, $OCF_3$, S($C_1-C_6$-alkyl), CN, $OCH_2$-phenyl, $NH_2$, NH—($C_1-C_6$-alkyl), N—($C_1-C_6$-alkyl)$_2$, piperidine, pyrrolidine, $CH_2F$, $CHF_2$, $OCH_2F$, $OCHF_2$, OH, $SO_2(C_1-C_6$-alkyl), C(O)$NH_2$, C(O)NH($C_1-C_6$-alkyl), and C(O)N($C_1-C_6$-alkyl)$_2$; or m, n and p are independently 0 or 1.

3. The compound of claim 1, wherein $R^1$ is H, methyl, (R)-methyl or (S)-methyl.

4. The compound of claim 1, wherein $R^1$ is H, methyl, (R)-methyl or (S)-methyl.

5. The compound of claim 3, wherein $R^2$ is H.

6. The compound of claim 5, wherein $R^5$ is H, methyl or (S)-methyl.

7. The compound of claim 6, wherein G is phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl or 4-($CH_2OPh$)-phenyl.

8. The compound of claim 7, wherein m is 1, n is 0 and p is 0, such that A is represented by the formula:

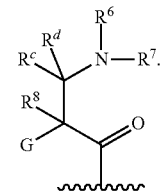

9. The compound of claim 8, wherein $R^8$ is H or OH.

10. The compound of claim 9, wherein $R_c$ and $R_d$ are H.

11. The compound of claim 10, wherein $R^6$ and $R^7$ are independently H, methyl, ethyl, isopropyl, isobutyl, tert-butyl, 3-pentyl, CH(isopropyl)$_2$, CH$_2$CH$_2$OH, CH$_2$CH$_2$CH$_2$OH, CH(CH$_2$CH$_2$OH)$_2$, CH$_2$CH$_2$OMe, CH(CH$_2$CH$_2$OMe)$_2$, CH$_2$CH$_2$CH$_2$OMe, CH$_2$CN, CH$_2$-cyclopropyl, CH$_2$-cyclobutyl, CH$_2$-t-butyl cyclopentyl, cyclohexyl, CH$_2$-phenyl, CH$_2$—(pyrid-2-yl), CH$_2$—(pyrid-3-yl), CH$_2$—(pyrid-4-yl), 4-hydroxycyclohex-1-yl, or CH(CH$_3$)CH(OH)phenyl.

12. The compound of claim 8, wherein A is selected from:

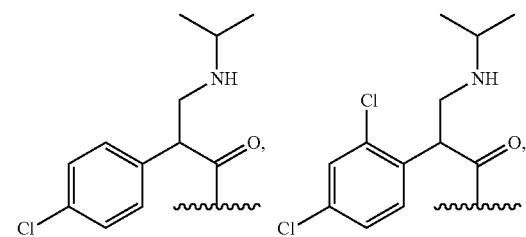
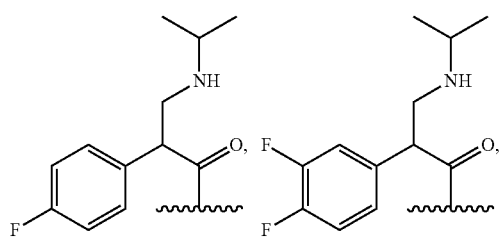
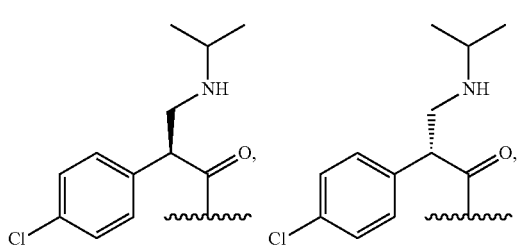
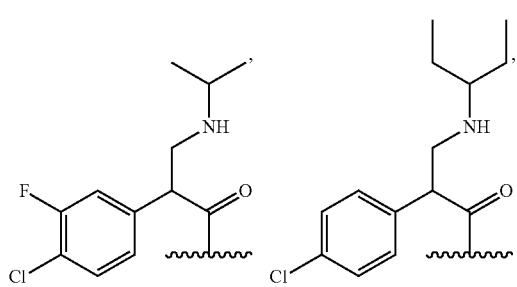
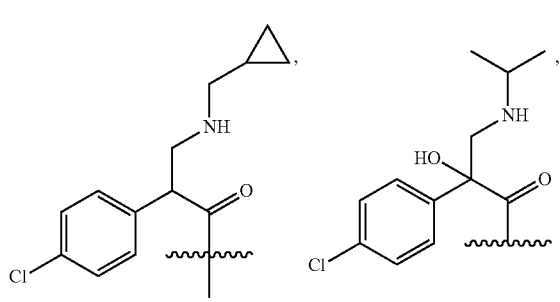

-continued

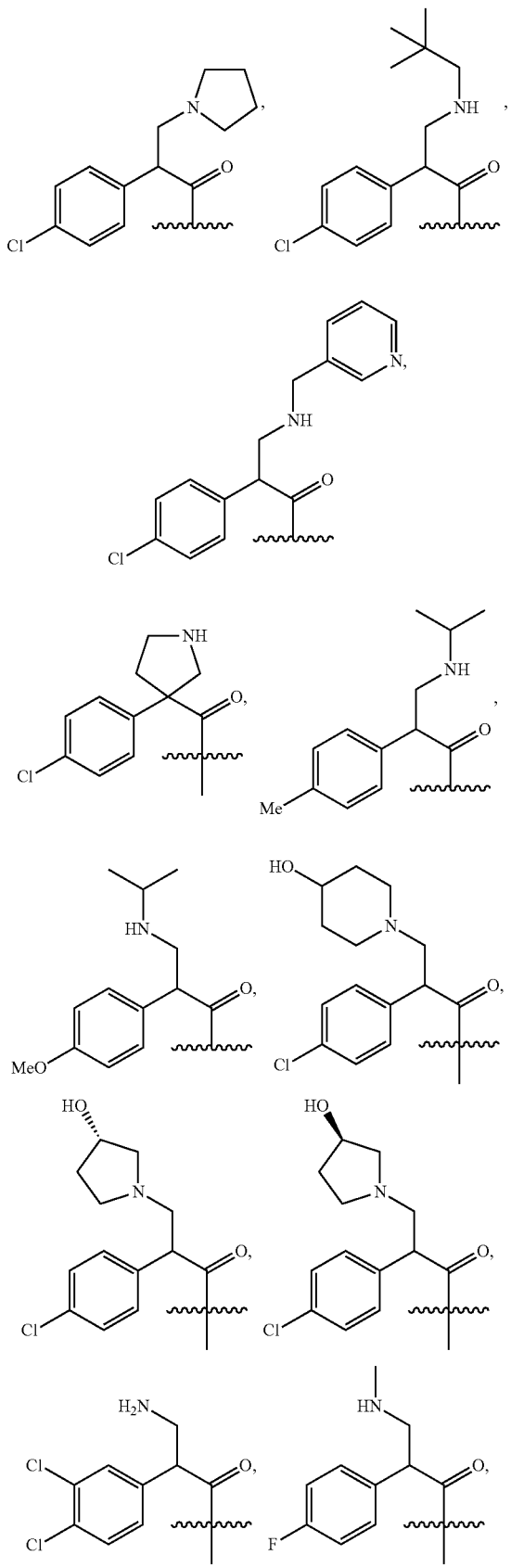

-continued

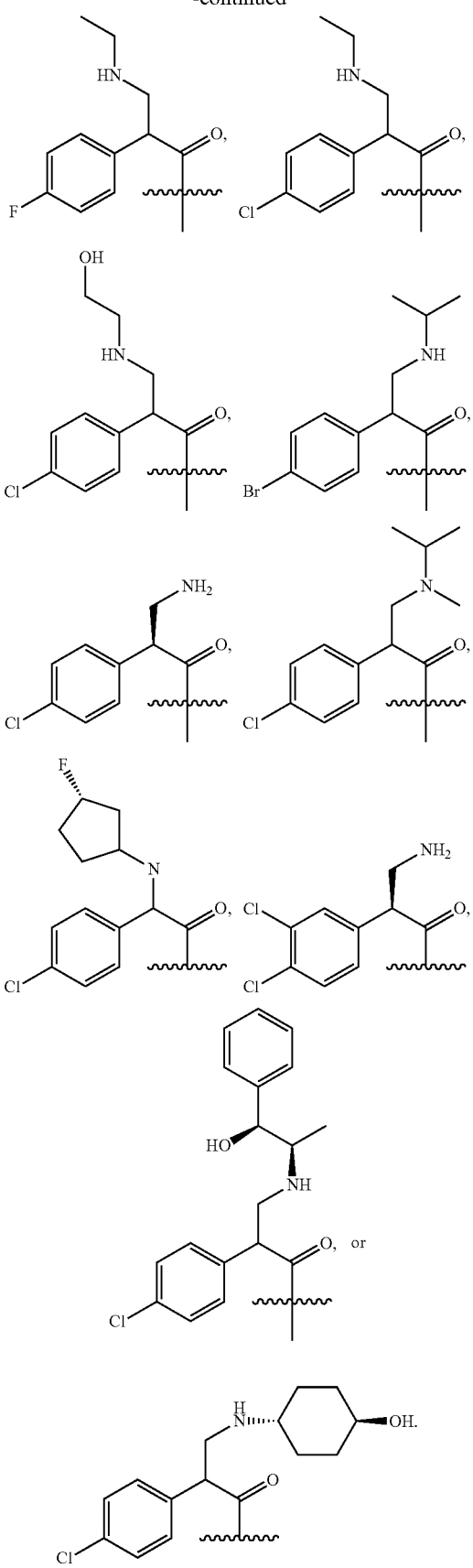

13. The compound of claim 7, wherein m is 1, n is 1 and p is 0, such that A is represented by the formula:

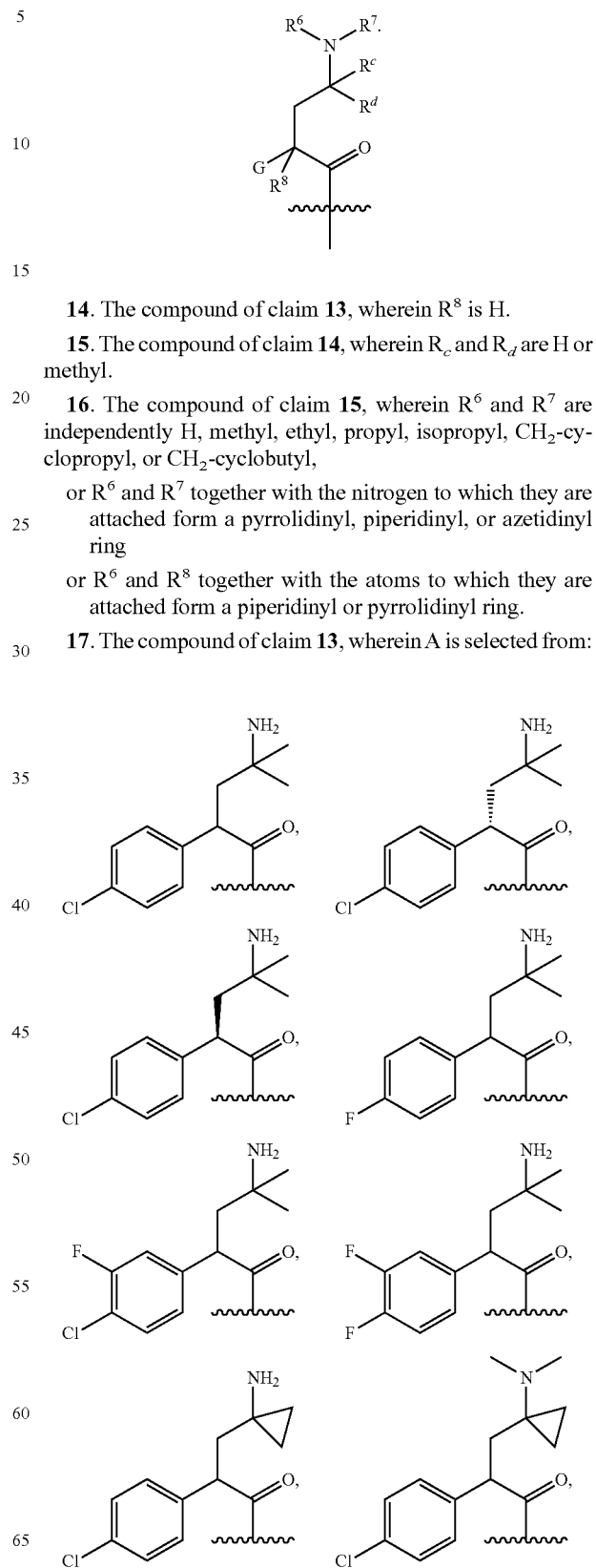

14. The compound of claim 13, wherein $R^8$ is H.

15. The compound of claim 14, wherein $R_c$ and $R_d$ are H or methyl.

16. The compound of claim 15, wherein $R^6$ and $R^7$ are independently H, methyl, ethyl, propyl, isopropyl, $CH_2$-cyclopropyl, or $CH_2$-cyclobutyl, or $R^6$ and $R^7$ together with the nitrogen to which they are attached form a pyrrolidinyl, piperidinyl, or azetidinyl ring or $R^6$ and $R^8$ together with the atoms to which they are attached form a piperidinyl or pyrrolidinyl ring.

17. The compound of claim 13, wherein A is selected from:

-continued

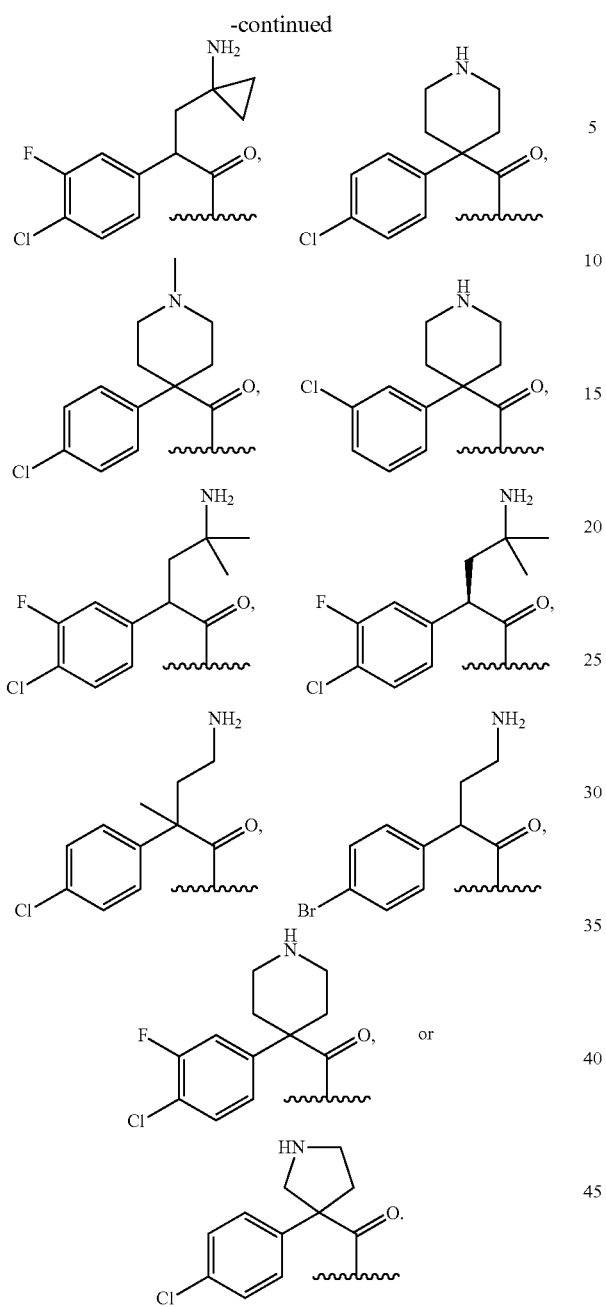

18. The compound of claim 7, wherein m is 1, n is 0 and p is 1, such that A is represented by the formula:

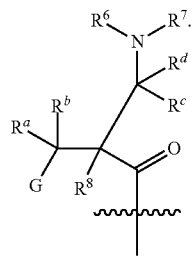

19. The compound of claim 18, wherein $R^8$ is H.

20. The compound of claim 19, wherein $R^6$ and $R^7$ are independently H, methyl, ethyl, propyl, isopropyl, t-butyl, $CH_2$-cyclopropyl, or $CH_2$-cyclobutyl.

21. The compound of claim 18, wherein A is selected from

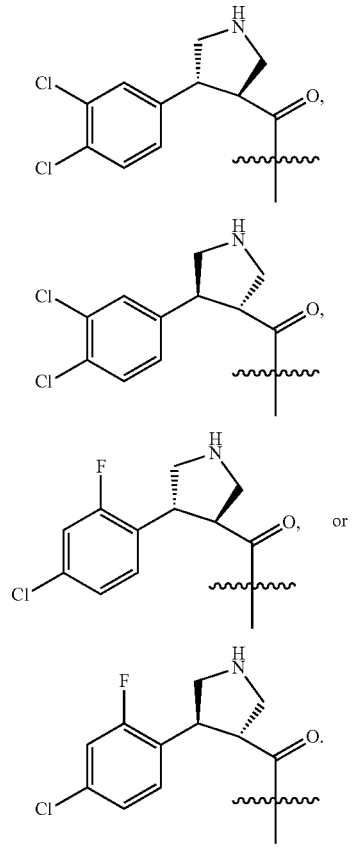

22. The compound of claim 7, wherein m is 0, n is 0 and p is 1, such that A is represented by the formula:

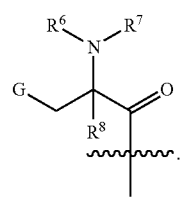

23. The compound of claim 22, wherein $R^8$ is H.

24. The compound of claim 23, wherein $R^6$ and $R^7$ are independently H or Me.

25. The compound of claim 24, wherein A is selected from:

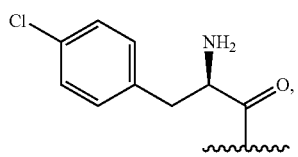

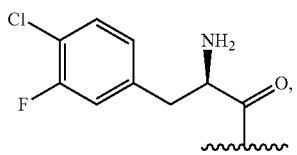
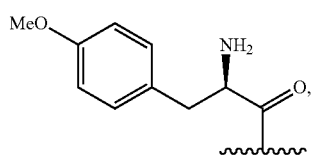
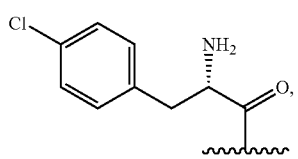
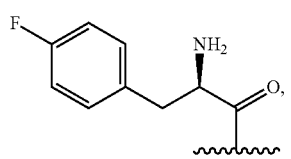
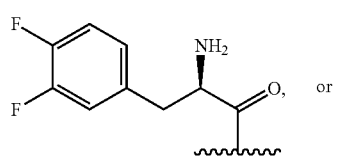, or
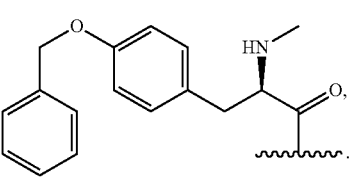.
26. A compound of claim 1 selected from the group consisting of:
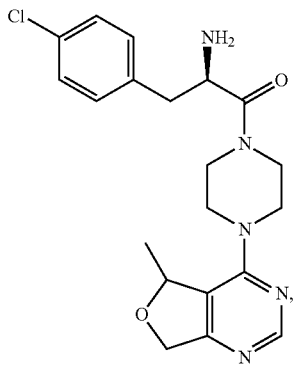
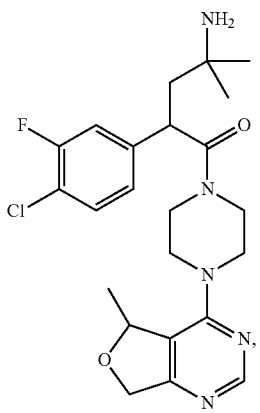
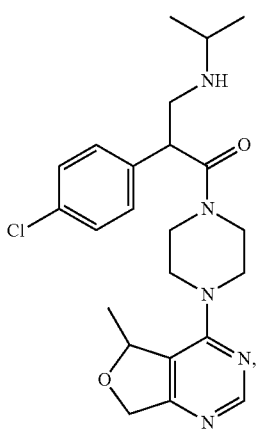
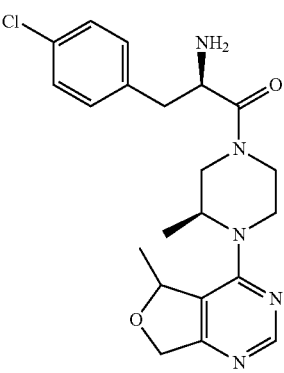
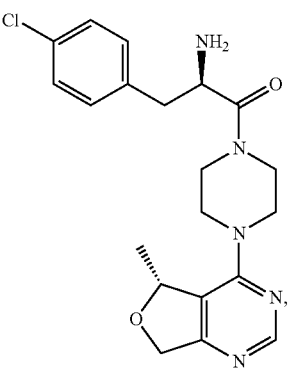

91
-continued
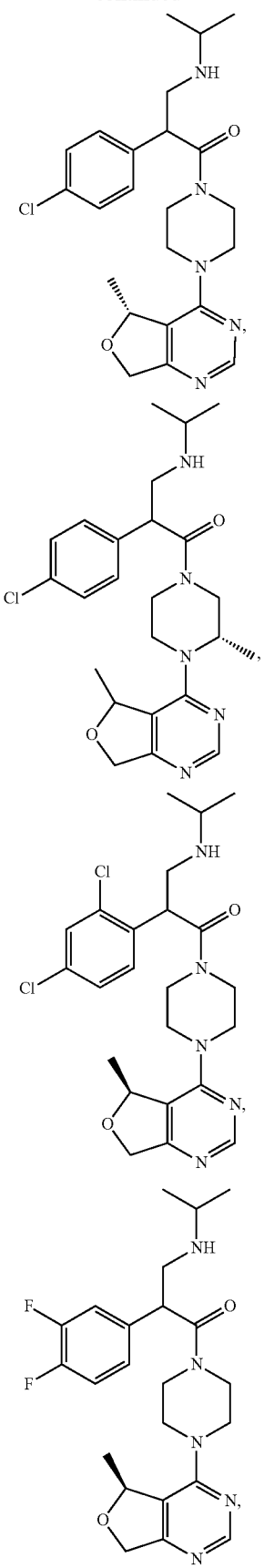
92
-continued
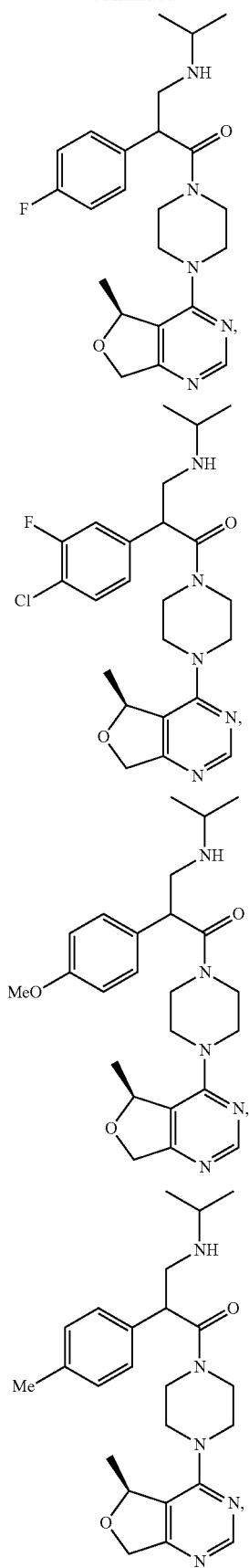

93
-continued
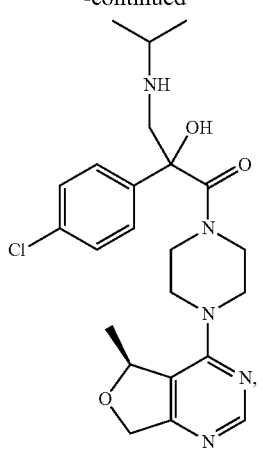
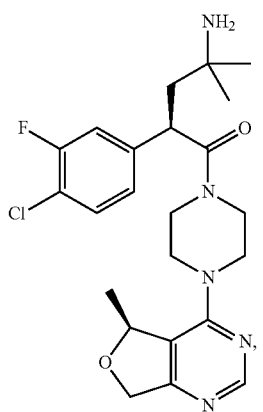
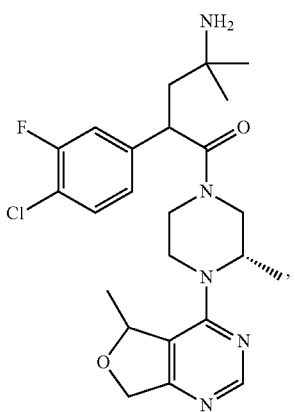
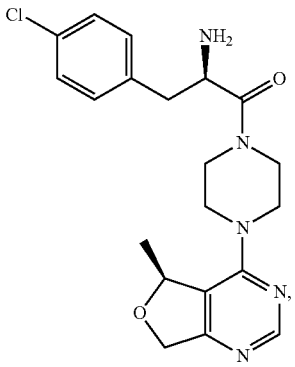
94
-continued
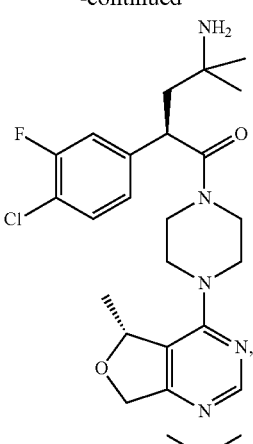
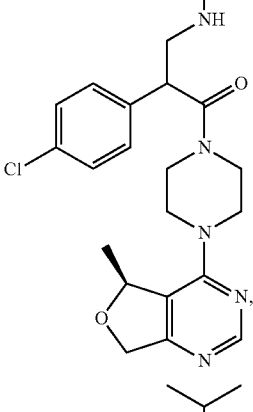
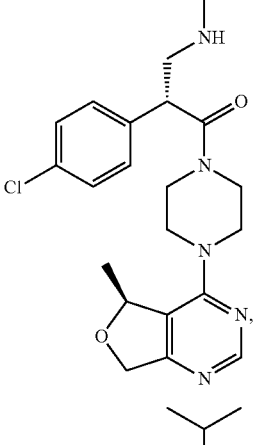
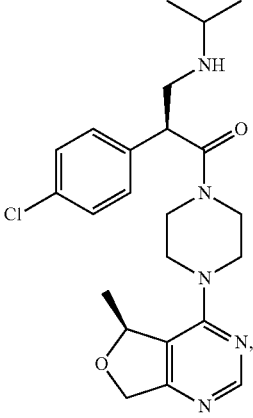

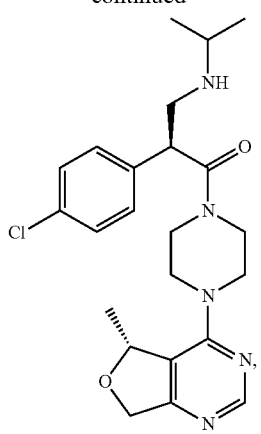
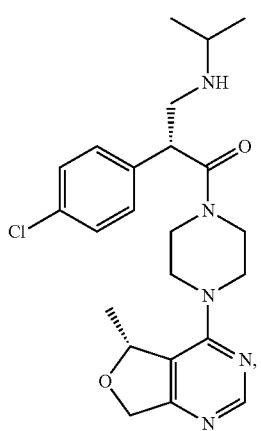
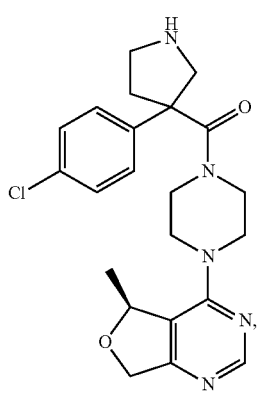
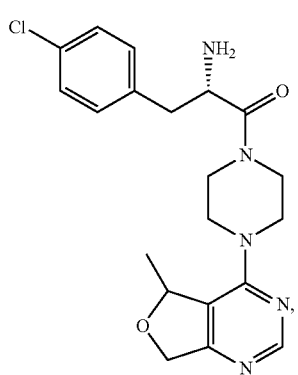
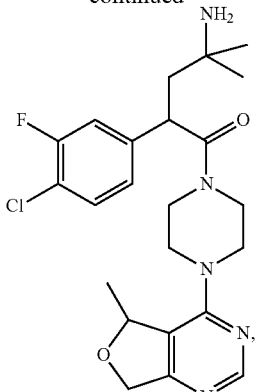
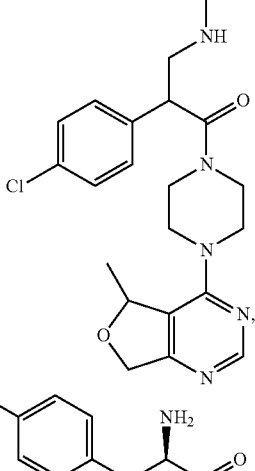
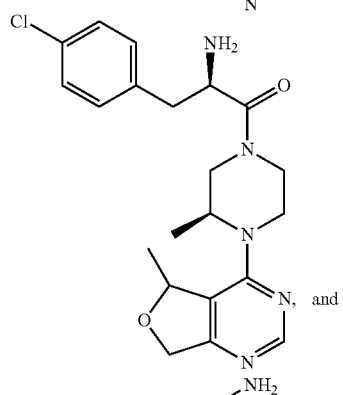
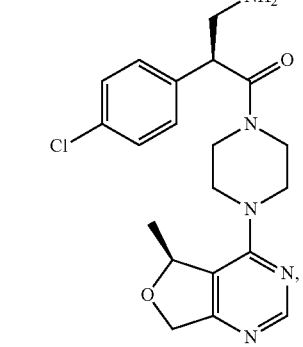
or a pharmaceutically acceptable salt thereof.
27. A pharmaceutical composition comprising of a compound as claimed in claim 1 and a pharmaceutically acceptable carrier.
* * * * *

UNITED STATES PATENT AND TRADEMARK OFFICE
CERTIFICATE OF CORRECTION

PATENT NO. : 8,329,701 B2  
APPLICATION NO. : 12/307537  
DATED : December 11, 2012  
INVENTOR(S) : Mitchell et al.

Page 1 of 1

It is certified that error appears in the above-identified patent and that said Letters Patent is hereby corrected as shown below:

In the Claims

Column 80, line 31, Claim 1

Replace:
thereof

With:
thereof,

Column 80, line 59, Claim 1

Replace:
cyclopropylmethyl, -$C_1$-$C_3$

With:
cyclopropylmethyl, $C_1$-$C_3$

Column 80, line 60-63, Claim 1

Replace:
or C(=O)($C_1$-$C_3$ alkyl) or $C_1$-$C_6$-alkyl optionally substituted with one or more groups independently selected from the group consisting of OH, O($C_1$-$C_6$-alkyl),

With:
or $C_1$-$C_6$-alkyl optionally substituted with one or more groups independently selected from the group consisting of OH, O($C_1$-$C_6$-alkyl), Signed and Sealed this  
Eighth Day of April, 2014

Michelle K. Lee  
*Deputy Director of the United States Patent and Trademark Office*